(12) United States Patent
Vainio et al.

(10) Patent No.: US 10,604,777 B2
(45) Date of Patent: Mar. 31, 2020

(54) METHOD OF PROCESSING LIGNOCELLULOSIC MATERIAL USING AN ALKALINE DELIGNIFICATION AGENT

(71) Applicant: NESTE OYJ, Espoo (FI)

(72) Inventors: Heidi Vainio, Espoo (FI); Ville Pihlajaniemi, Helsinki (FI); Mika Sipponen, Espoo (FI); Ossi Pastinen, Kantvik (FI); Ilkka Lehtomäki, Helsinki (FI); Simo Laakso, Turku (FI); Olavi Myllymäki, Espoo (FI); Perttu Koskinen, Helsinki (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 15/103,764

(22) PCT Filed: Dec. 11, 2014

(86) PCT No.: PCT/EP2014/077464
§ 371 (c)(1),
(2) Date: Jun. 10, 2016

(87) PCT Pub. No.: WO2015/086782
PCT Pub. Date: Jun. 18, 2015

(65) Prior Publication Data
US 2016/0312259 A1 Oct. 27, 2016

(30) Foreign Application Priority Data
Dec. 11, 2013 (EP) .................................. 13196744

(51) Int. Cl.
*C12P 19/14* (2006.01)
*C12P 19/02* (2006.01)
*C12P 7/64* (2006.01)

(52) U.S. Cl.
CPC .............. *C12P 19/14* (2013.01); *C12P 7/64* (2013.01); *C12P 19/02* (2013.01); *C12P 2201/00* (2013.01)

(58) Field of Classification Search
None
See application file for complete search history.

(56) References Cited

U.S. PATENT DOCUMENTS

| | | | |
|---|---|---|---|
| 7,691,792 B1 | 4/2010 | Fisher et al. | |
| 2008/0032344 A1 | 2/2008 | Fallavollita | |
| 2009/0004715 A1 | 1/2009 | Trimbur et al. | |
| 2009/0011480 A1 | 1/2009 | Trimbur et al. | |
| 2009/0035842 A1 | 2/2009 | Trimbur et al. | |
| 2009/0047721 A1 | 2/2009 | Trimbur et al. | |
| 2009/0061493 A1 | 3/2009 | Trimbur et al. | |
| 2009/0061495 A1* | 3/2009 | Beatty ................... | C12P 7/10 435/165 |
| 2009/0148918 A1 | 6/2009 | Trimbur et al. | |
| 2010/0323413 A1 | 12/2010 | Trimbur et al. | |
| 2010/0323414 A1 | 12/2010 | Trimbur et al. | |
| 2011/0014665 A1 | 1/2011 | Trimbur et al. | |
| 2011/0015417 A1 | 1/2011 | Trimbur et al. | |
| 2011/0047863 A1 | 3/2011 | Trimbur et al. | |
| 2011/0190522 A1 | 8/2011 | Trimbur et al. | |
| 2011/0217745 A1 | 9/2011 | Li et al. | |
| 2011/0252696 A1 | 10/2011 | Franklin et al. | |
| 2011/0262970 A1 | 10/2011 | Li et al. | |
| 2011/0314726 A1 | 12/2011 | Jameel et al. | |
| 2012/0028319 A1 | 2/2012 | Trimbur et al. | |
| 2012/0036768 A1 | 2/2012 | Phillips et al. | |
| 2012/0122192 A1 | 5/2012 | Trimbur et al. | |
| 2012/0159838 A1 | 6/2012 | Malm et al. | |
| 2012/0159839 A1 | 6/2012 | Koskinen et al. | |
| 2012/0159840 A1 | 6/2012 | Koskinen et al. | |
| 2012/0164701 A1 | 6/2012 | Trimbur et al. | |
| 2012/0288930 A1 | 11/2012 | Trimbur et al. | |
| 2013/0143285 A1* | 6/2013 | Tolan ...................... | C08H 8/00 435/136 |
| 2013/0330790 A1 | 12/2013 | Trimbur et al. | |
| 2014/0170716 A1 | 6/2014 | Trimbur et al. | |
| 2014/0234919 A1 | 8/2014 | Yu et al. | |

FOREIGN PATENT DOCUMENTS

| | | |
|---|---|---|
| EP | 1 396 531 A2 | 3/2004 |
| EP | 1 398 364 A1 | 3/2004 |
| EP | 1 741 767 A1 | 1/2007 |
| EP | 1 741 768 A1 | 1/2007 |
| EP | 2 468 857 A1 | 6/2012 |
| EP | 2 468 875 A1 | 6/2012 |
| EP | 2 468 877 A1 | 6/2012 |

(Continued)

OTHER PUBLICATIONS

McIntosh et al., "Optimisation of dilute alkaline pretreatment for enzymatic saccharification of wheat straw", Biomass and Bioenergy 2011, vol. 35, pp. 3094-3103.*
International Search Report (PCT/ISA/210) dated Feb. 16, 2015, by the Japanese Patent Office as the International Searching Authority for International Application No. PCT/EP2014/077462.
Written Opinion (PCT/ISA/237) dated Feb. 16, 2015, by the Japanese Patent Office as the International Searching Authority for International Application No. PCT/EP2014/077462.

(Continued)

*Primary Examiner* — Michelle F. Paguio Frising
(74) *Attorney, Agent, or Firm* — Buchanan Ingersoll & Rooney PC

(57) ABSTRACT

The present disclosure relates to a method for obtaining sugar and lignin fractions from lignocellulosic materials and to a method for producing fermentation products using the sugars obtained from the lignocellulose. The present disclosure relates to a method for improving the sugar yield in the enzymatic hydrolysate by introducing a pre-treatment step of hydrothermal hydrolysis and an alkaline delignification step.

12 Claims, 13 Drawing Sheets

(56) References Cited

FOREIGN PATENT DOCUMENTS

| WO | WO 01/32715 A1 | 5/2001 |
|---|---|---|
| WO | WO 2008/151149 A2 | 12/2008 |
| WO | WO 2010/025455 A2 | 3/2010 |
| WO | WO 2010/039783 A2 | 4/2010 |
| WO | WO 2010/060052 A2 | 5/2010 |
| WO | WO 2012/085340 A1 | 6/2012 |
| WO | WO 2013/006755 A2 | 1/2013 |

OTHER PUBLICATIONS

International Search Report (PCT/ISA/210) dated Jan. 28, 2015, by the Japanese Patent Office as the International Searching Authority for International Application No. PCT/EP2014/077464.
Written Opinion (PCT/ISA/237) dated Jan. 28, 2015, by the Japanese Patent Office as the International Searching Authority for International Application No. PCT/EP2014/077464.
International Search Report (PCT/ISA/210) dated Feb. 12, 2015, by the Japanese Patent Office as the International Searching Authority for International Application No. PCT/EP2014/077465.
Written Opinion (PCT/ISA/237) dated Feb. 12, 2015, by the Japanese Patent Office as the International Searching Authority for International Application No. PCT/EP2014/077465.
Barcelos, C.A. et. al., "The Essentialness of Delignification on Enzymatic Hydrolysis of Sugar Cane Bagasse Cellulignin for Second Generation Ethanol Production", Waste and Biomass Valorization, Jun. 21, 2012, pp. 341-346, vol. 4, No. 2. XP055117486.
Irfan et al., "Effect of Various Pretreatment Conditions on Enzymatic Saccharification", Songklanakarin Journal of Science and Technology, Jul.-Aug. 2011, pp. 397-404, vol. 33, No. 4. XP055117426.
Huang, C. et al., "Microbial Oil Production From Rice Straw Hydrolysate by *Trichosporon fermentans*", Bioresource Technology, Oct. 1, 2009, pp. 4535-4538, vol. 100, No. 19. XP026148880.
Chen et al., "Microbial Oil Production From Corncob Acid Hydrolysate", Biotechnology Letters, Feb. 16, 2012, pp. 1025-1028, vol. 34, No. 6. XP035047251.
Yu, X. et al., "Oil Production By Oleaginous Yeasts Using The Hydrolysate From Pretreatment Of Wheat Straw With Dilute Sulfuric Acid", Bioresource Technology, Feb. 18, 2011, No. 10, pp. 6134-6140, vol. 102. XP028407881.
Ruan, Z. et al., "Evaluation of lipid accumulation from lignocellulosic sugars by *Mortierella isabellina* for biodiesel production", Bioresource Technology, Jan. 28, 2012, pp. 198-205, vol. 110.
Yousuf, A., "Biodiesel from lignocellulosic biomass—Prospects and challenges", Waste Management, Apr. 3, 2012, pp. 2061-2067, vol. 32, No. 11.
Tanaka, M. et al., "Removal of Lignin and Reuse of Cellulases for Continuous Saccharification of Lignocellulos", Biotechnology and Bioengineering, 1988, pp. 897-902, vol. 32.
Harmsen, P. et al., "Literature review of physical and chemical pretreatment processes for lignocellulosic biomass", Wageningen UR Food and Biobased Research, Sep. 2010, pp. 1-48, retrieved from the internet: http://www.biomassandbioenergy.nl/filesdwnld/Literature%20review_FBR.pdf.
Alvira, P. et al., "Pretreatment technologies for an efficient bioethanol production process based on enzymatic hydrolysis: A review", Bioresource Technology, Dec. 29, 2009, pp. 4851-4861, vol. 101, No. 13.
Huang, HJ et al., "A review of separation technologies in current and future biorefineries", Separation and Purification Technology, Aug. 2008, pp. 1-21, vol. 62, No. 1.

\* cited by examiner

FIG. 13

Table 1

| Delignification treatment | Amount of alkaline chemical[a] | pH before treatment[b] | pH after treatment[c] | DM yield[d] | Monomeric sugar yield based on delignified straw DM[e] | Sugar yield based on autohydrolyzed straw DM (%)[f] | Sugar yield based on autohydrolyzed straw carbohydrates (%)[g] |
|---|---|---|---|---|---|---|---|
| NaOH + 2% $H_2O_2$ solution | 3.3 | 10.2 | 8.5 | 77 | 0.48 | 37.0 | 63.1 |
| $Ca(OH)_2$ | 3 % saturated solution | 10.30 | 9.3 | 91 | 0.41 | 37.3 | 63.7 |
| $Ca(OH)_2$ + 1% $H_2O_2$ solution | 3 % saturated solution | 9.30 | 7.8 | 91 | 0.42 | 38.2 | 65.2 |
| NaOH | 0.85 | 10.0 | 8.8 | 89 | 0.44 | 39.5 | 67.4 |
| AH straw without delignification | 0 | 5.2 | 5.3 | 100 | 0.36 | 36.0 | 61.4 |

[a] % of autohydrolyzed straw on dry matter basis
[b] pH of the liquor before heating
[c] pH of the liquor after heating and filtration of solids
[d] % dry matter left after delignification treatment
[e] ratio of monomeric sugars obtained from enzymatic hydrolysis to dry matter of delignified straw g/g basis
[f] ratio of sugars obtained from enzymatic hydrolysis to dry matter of autohydrolyzed straw
[g] calculated as the ratio of total amount of monosaccharides released in enzymatic hydrolysis to total amount of mosaccharides released from similar weight of autohydrolyzed straw in acid hydrolysis multiplied with the dry matter yield from the delignification treatment

METHOD OF PROCESSING LIGNOCELLULOSIC MATERIAL USING AN ALKALINE DELIGNIFICATION AGENT

FIELD OF THE INVENTION

The present invention relates to a method for obtaining sugar and lignin fractions from lignocellulosic materials and to a method for producing fermentation products using the sugars obtained from the lignocellulose.

BACKGROUND OF THE INVENTION

Lignocellulose is the most abundant biopolymer on earth. Lignocellulose is the major structural component of woody plants and non-woody plants such as grass. Lignocellulosic biomass refers to plant biomass that is composed of cellulose, hemicellulose, and lignin. Large amounts of lignocellulosic residues are produced through forestry, timber and pulp and paper industries and agricultural practices (e.g. straw, stover, sugar cane bagasse, chaff, hulls) and many agroindustries. Also municipal waste contain fractions that can be considered as lignocellulose residues, such as paper or cardboard waste, garden waste or waste wood from construction. Lignocellulosic residues, such as agricultural residues, offer highly sustainable, non-food and non-ILUC (indirect land use change), alternative for production of biofuels. In addition, due to high abundance and low price lignocellulosic residues are preferred materials for production of biofuels. In addition, dedicated woody or herbaceous energy crops with biomass productivity have gained interest as biofuel use.

The production of biofuels, especially ethanol, from lignocellulosic materials by microbial fermentations has been studied extensively. The greatest challenge for utilization of lignocellulosics for microbiological production of biofuels or biofuel feedstocks lays in the complexity of the lignocellulose material and in its resistance to biodegradation. In lignocellulose, cellulose (20-50% of plant dry weight) fibers are embedded in covalently found matrix of hemicellulose (20-40%), pectin (2-20%) and lignin (10-25%) forming very resistant structure for biodegradation. Further, the sugar residues of hemicellulose contain a varying mixture of hexoses (e.g., glucose, mannose and galactose), and pentoses (e.g., arabinose and xylose) depending on the biomass.

Certain microorganisms can produce lipids from organic molecules, such as sugars derived from lignocellulose. Certain microorganisms, typically yeast, fungi or bacteria, can efficiently convert both C6 and C5 sugars in lignocellulosic materials to oil. Oil produced by heterotrophic microorganisms is often called as single cell oil or microbial oil. Single cell oil production process using heterotrophic microorganisms typically comprises cultivating microorganisms in aerated bioreactors, allowing cells to accumulate lipids, harvesting lipid-rich cells and recovering oil from cells. Microorganism-based lipids (i.e. single cell oils) can be used as raw materials for production of biofuels such as biodiesel, renewable diesel or bio jet fuel.

The economically feasible production of biofuels from lignocellulosic materials by microbial fermentation requires an efficient conversion of all the main carbohydrate constituents of the lignocellulosic materials to biofuels. On the other hand the economic feasibility of the biofuel production requires that all the main carbohydrate constituents of the lignocellulosic material have to be converted to sugars, which are suitable for microbial production. Generally this means breaking (hydrolyzing) the polymeric structures of hemicellulose and cellulose to obtain monomeric sugars.

The prior art discloses several methods, which can be used for production of sugars from lignocellulosic materials.

Patent publication US2008/032344 A1 discloses a process for recovery of cellulosic sugars and near native lignin co-product from lignocellulosic biomass. The process comprises subjecting the raw material to autohydrolysis, organosolv and enzymatic hydrolysis treatments to produce a cellulosic sugar solution comprising glucose, which is fermented with yeast and/or appropriate recombinant organism to produce biofuel and/or chemical.

Cunningham and Carr (1984) have reported various technologies to remove hemicellulose and lignin from wheat straw to provide an upgraded cellulosic residue for enzymatic hydrolysis. They have also disclosed a pre-treatment method comprising autohydrolysis of the wheat straw followed by subsequent alkali treatment with NaOH. The amount of NaOH used in delignification of autohydrolyzed wheat straw is significantly higher than in the present invention. According to the teachings of Cunningham and Carr the delignification treatment of autohydrolysed straw did not significantly improve the cellulose conversion to glucose in the enzymatic treatment step whereas alkali treatment without autohydrolysis step significantly improved the results of the enzymatic hydrolysis (see Tables III and IV). Furthermore the obtained hemicellulose and cellulose hydrolysates are not used in production of single-cell oil as in the present invention.

Patent publication US 2013/143285 A1 describes a process for conversion of lignocellulosic feedstock to fermentable sugars. The process comprises subjecting the lignocellulosic feedstock to alkali-treatment at a pH of 8-12, to a dilute acid treatment and finally to enzymatic hydrolysis to produce sugar solution comprising glucose, which is fermented to a fermentation product.

Patent publication US 2012/036768A1 describes a method for producing fermentable sugars from lignocellulosic materials, in which method a pre-treated lignocellulosic material is subjected to two-stage enzymatic hydrolysis treatment. The first enzymatic treatment comprises a mixing the pre-treated material with a first enzymatic composition to produce a first hydrolysis mixture, which is thickened to increase the fiber concentration to provide a second hydrolysis mixture. The second enzymatic treatment comprises mixing the second hydrolysis mixture with a second enzymatic composition to produce a liquid mixture containing fermentable sugars and a solid lignin phase.

One of the major challenges in production of lignocellulosic sugars from lignocellulosic material is to provide a process, which enables cost-efficient production of high quality sugar hydrolysates, which can be used without further purification in production of single-cell oil. The high quality of the sugar hydrolyzates means that the amount of impurities such as phenols and acids should be below the concentration, which is toxic to the microorganism used in the fermentation. The cost efficiency requires that the consumption of hydrolysation agents such as enzymes should be kept at low level. This can be achieved for example by recycling of the cooking chemicals. The economic feasibility requires that the quality of the side streams, which are not used as raw material for microbial fermentation, should be as high as possible to enable the valorization of these streams.

State-of-the-art lignocellulose pre-treatment technologies have been designed for anaerobic fermentations (cellulosic ethanol). Microbial oil production differs from anaerobic fermentations since it is aerobic process (requires oxygen). This invention describes a lignocellulose fractionation process that has benefits especially for aerobic bioprocesses, such as microbial oil production.

SUMMARY OF THE INVENTION

It is one object of the present invention to provide a lignocellulose fractionation process, which enables production of high quality sugar hydrolysates usable as carbon source in production of microbial oil with heterotrophic microorganisms.

Another object of the present invention is to provide a fractionation process with improved yield and productivity of the enzymatic hydrolysis of cellulose fractions.

A third object of the present invention is to provide a fractionation process, which produces a high quality lignin fraction.

A fourth object of the present invention is to provide a fractionation method, which has an improved cost-efficiency of the aerobic fermentation process due to the low amount of inert material (lignin) and inhibitor compounds in the sugar fraction used in aerobic fermentation.

To achieve the above state objects, the invention is characterized by the features defined in the independent claims.

In a first aspect of the present invention relates to a method for fractionation of a lignocellulosic material, the method comprising
  a) Subjecting the lignocellulosic material to a treatment wherein hemicellulose is at least partially removed from the lignocellulosic material to produce a mixture comprising a first liquid phase and a first solid phase,
  b) Separating the first solid phase from the first liquid phase,
  c) Subjecting the first solid phase to a delignification treatment in the presence of alkaline delignification agent to produce a mixture comprising a second solid phase and a second liquid phase containing solubilized lignin,
  d) Separating the second solid phase from the second liquid phase,
  e) Subjecting the second solid phase to an enzymatic hydrolysis treatment in the presence of enzymes capable of hydrolyzing the hemicellulose and cellulose fractions of the second solid phase to produce a mixture comprising a third liquid phase and a third solid phase.

A second aspect of the present invention relates to a liquid phase in the form of an enzymatic hydrolysate obtainable by the method of the present invention (the third liquid phase).

A third aspect of the present invention a concentrated sugar hydrolysate obtainable by the method of the present invention.

A fourth aspect relates to a precipitated lignin fraction obtainable by the method of the invention.

A further aspect of the present invention relates to a method for production of microbial lipid, the method comprising
  (i) providing a cultivation medium comprising the enzymatic hydrolysate liquid phase obtained by method for fractionation of a lignocellulosic material (the third liquid phase) or the concentrated sugar hydrolysate of the present invention,
  (ii) providing a fermentation broth by inoculating the cultivation medium with an oleaginous microbe,
  (iii) incubating said medium inoculated with said oleaginous microbe allowing lipid to accumulate,
  (vi) recovering the lipid from said oleaginous microbe.

Other preferred embodiments are presented in dependent claims.

The invention is based on the findings that by performing treatment that dissolves hemicellulose and by separating lignin prior to enzymatic hydrolysis step by alkali treatment, the total sugar yield increases. This is important since the object of the invention is to extract as much sugars as possible from the lignocellulosic material. Another advantage of the invention is that the efficiency of the enzymatic hydrolysis and the cost-efficiency of the aerobic fermentation are significantly improved.

The invention is also based on another finding that the alkali treatment can be conducted with a very low amount of alkali agent compared to prior art disclosures.

The invention is also based on a finding that the hemicellulosic sugars separated from the lignocellulosic material before delignification can be used in microbial fermentation without any purification treatment.

The present invention provides the following advantages:
  high total sugar yield, both cellulosic and hemicellulosic sugars are efficiently recovered
  more efficient enzymatic hydrolysis of cellulose fraction in terms of sugar yield and productivity,
  production of high quality lignin fraction, which enables lignin valorization
  increase cost efficiency of the aerobic fermentation process,
  production of high quality microbial biomass residue from aerobic fermentation comprising low amount of lignin, which enables use of the residue as an animal feed,
  decreased consumption of alkaline agent in delignification and subsequently decrease consumption of acid in the precipitation of dissolved lignin and in the pH adjustment prior to enzymatic hydrolysis.

BRIEF DESCRIPTION OF THE DRAWINGS

FIG. 13 Table 1. Comparison of dry matter yield (DM yield) from autohydrolyzed straw with different delignification treatments. Sugar yield from enzymatic hydrolysis of delignified straw was dependent on treatment conditions. Sugar yield below is given both based on dry matter of autohydrolysed straw and based on carbohydrate content of autohydrolysed straw.

Figure 1:
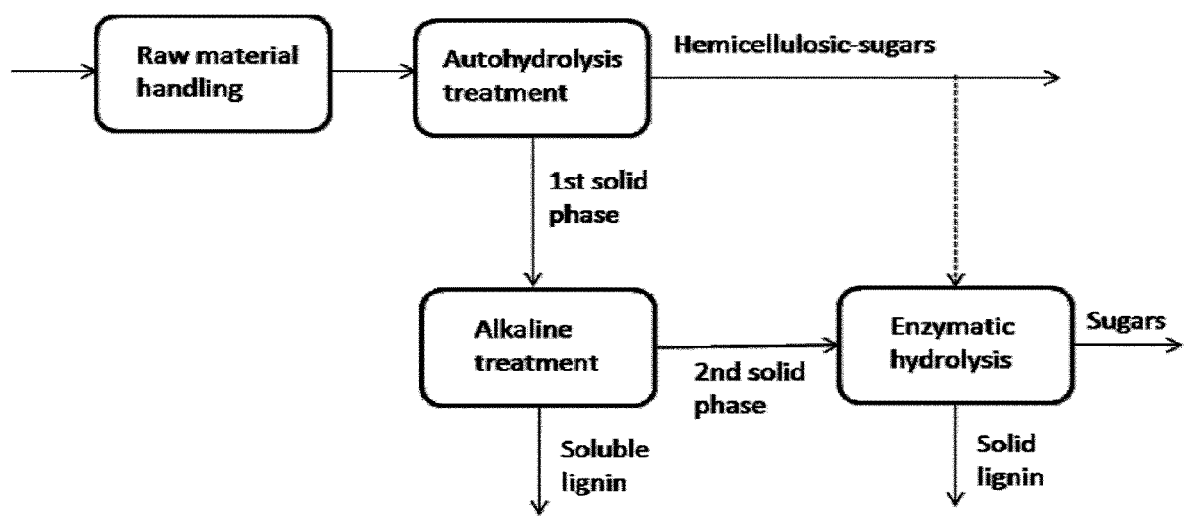
FIG. 1, FIG. 2, FIG. 3, and FIG. 4 present the process schemes of the according to the embodiments of the invention.

Table 2: Composition of growth medium before feeds

Table 3: Composition of inoculation medium, pH set to 5.5.

Table 4: Composition of fermentation medium

DETAILED DESCRIPTION OF THE INVENTION

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

Definitions

Lignocellulosic Material

The terms "lignocellulosic biomass" or "lignocellulosic material" is meant to include but is not limited to woody plants or non-woody, herbaceous plants or other materials containing cellulose and/or hemicellulose: Materials can be agricultural residues (such as wheat straw, rice straw, chaff, hulls, corn stover, sugarcane bagasse, sugar cane tops and leaves), dedicated energy crops (such as switchgrass, *Miscanthus, Arundo donax*, reed canary grass, willow, water hyacinth, energy cane, energy sorghum), wood materials or residues (including sawmill and pulp and/or paper mill residues or fractions, such as hemicellulose, spent sulphite liquor, waste fibre and/or primary sludge), moss or peat, or municipal paper waste. The term lignocellulosic material comprises also low lignin materials, materials such as macroalgae biomass. In addition, the materials comprise also hemicellulose or cellulose fractions from industrial practises. The term lignocellulosic material encompasses any kind of cellulose fraction. The raw materials or certain fractions, such as hemicellulose and/or cellulose, of raw materials from different origin, plant species, or industrial processes can be mixed together and used as raw materials for cultivating microorganism biomass according to this disclosure. Typically the lignin content in lignocellulose is higher than 5%. Lignocellulosic biomass may also contain starch, e.g. in the case of whole plants Hydrolysis The term "hydrolysis" refers here to depolymerisation by addition of water into glycosidic linkages or ester linkages of non-monomeric carbohydrates to sugar oligomers and monomers or carboxylic acids.

Hydrolysate

The terms "hydrolysate" or "hydrolysed material" refers here to material that has undergone hydrolysis.

Lignocellulose Hydrolysate

The term "lignocellulose hydrolysate" refers here to hydrolysis products of lignocellulose or lignocellulosic material comprising cellulose and/or hemicellulose, oligosaccharides, mono- and/or disaccharides, acetic acid, formic acid, other organic acids, furfural, hydroxymethyl furfural, levulinic acid, phenolic compounds, other hydrolysis and/or degradation products formed from lignin, cellulose, hemicellulose and/or other components of lignocellulose, nitrogen compounds originating from proteins, metals and/or non-hydrolysed or partly hydrolysed fragments of lignocellulose.

Aromatic Compounds, Phenolic Compounds

Aromatic hydrocarbon refers here to a compound having a ring structure, formed by covalent linkages between carbon atoms, that contains alternating conjugated double and single bonds in a ring structure. Aromatic hydrocarbon can also refer to a compound having a ring structure, formed by covalent linkages between carbon atoms and non-carbon atoms, that contains alternating conjugated double and single bonds in a ring structure.

The term "phenolic compound" refers here to a compound comprising at least one aromatic hydrocarbon group containing at least one hydroxyl group (—OH) bonded directly to the aromatic hydrocarbon group. In this application the phenolic compound concentration has been measured with colorimetric analysis according to the Folin-Ciocalteu method (Waterhouse, 2002). Such compounds include, but are not limited to phenolic compounds such as p-coumaryl alcohol, coniferyl alcohol, sinapyl alcohol, 4-hydroxyacetophenone, acetovanillone, acetosyringone, 4-hydroxybenzaldehyde, vanillin, syringaldehyde, 4-hydroxybenzoic acid, vanillic acid, syringic acid, p-coumaric acid, ferulic acid, sinapic acid, phenol, guaiacol, syringol, hydroquinone, catechol, 2-methylphenol, 3-methylphenol, 4-methylphenol, 2,6-dimethylphenol, 2,4-dimethylphenol, 4-ethylphenol, 3,4-dihydroxybenzaldehyde, 4-methylguaiacol, 4-vinylphenol, 4-ethyl-2-methylphenol, 4-allylphenol, 3-methoxycatechol, 2,6-dimethoxy-4-methylphenol, vanillyl alcohol, homovanillin, homovanillic acid, 1-(4-hydroxy-3-methoxyphenyl)ethanol, 1-(4-hydroxy-3-methoxyphenyl)allene, vanillic acid methyl ester, 4-ethyl-2,6-dimethoxyphenol, 4-methylcatechol, 4-ethylguaiacol, 4-propylphenol, 4-vinylguaiacol, 4-hydroxybenzyl alcohol, 3-hydroxy-2-methyl-(4H)-pyran-4-one, 3,5-dihydroxy-2-methyl-(4H)-pyran-4-one, 4-propenylphenol, 2,6-dimethoxy-4-propylphenol, dihydroconiferyl alcohol, homosyringaldehyde, 3,5-dimethoxy-4-hydroxybenzyl alcohol, 2,6-dimethoxy-4-propenylphenol, 1-(3,5-dimethoxy-4-hydroxyphenyl)ethanol, coniferyl aldehyde, syringylacetone, syringic acid methyl ester, propiosyringone, syringyl vinyl ketone, dihydrosinapyl alcohol, sinapaldehyde, 2,6-dimethoxyphenol, 1-(4-hydroxyphenyl)ethanol, eugenol, 5-ethylpyrogallol, 4-propylguaiacol, 1,4-dihydroxy-3-methoxybenzene, isoeugenol, 4-hydroxybenzoic acid methyl ester, guaiacylacetone, 2,6-dimethoxy-4-vinylphenol, propiovanillone, guaiacyl vinyl ketone, 4-allyl-2,6-dimethoxyphenol, and including all their possible isomers, oligomeric and/or polymeric lignin, tannins, polyphenols, mixtures of phenolic compounds, covalently linked compounds comprising non-phenolic compounds and phenolic compounds.

The term "concentration of phenolic compounds" is meant the concentration of compounds (typically expressed as g/l) in aqueous solution as measured with the Folin-Ciocalteu method (Waterhouse, 2002)

Hydrothermal Treatment

In the context of the present invention the term "hydrothermal treatment" refers to heat treatment of aqueous lignocellulose suspension at temperatures exceeding 50° C. Hydrothermal treatment can be carried out under pressure in a pressurized reactor or at atmospheric pressure in a non-pressurized reactor. The pressure in pressurized reactor may be generated by steam obtained from the water when heated up to boiling point or by added pressurized gas phase. Hydrothermal treatment may be carried out in the presence of a catalyst or in the absence of a catalyst. Hydrothermal treatment in the absence of a catalyst (also referred to as "autohydrolysis" or "AH") to hydrolysis of lignocellulosic biomass without added catalyst when aqueous suspension of lignocellulosic biomass is subjected to hydrothermal treatment at temperatures exceeding 120° C. under pressure.

"Autohydrolysed straw" refers here to solid fraction that has been obtained after autohydrolysis of straw. Autohydrolysed straw may have been subjected to washing.

Severity

The term "severity" refers here to factor, which is calculated by equation 1 and which describes the hydrothermal conditions in terms of temperature and reaction time.

$$S=\text{Log}(R_0),$$

where $R_0 = \int_0^t \exp((T(t)-Tr)/14.7)] \, dt$ and $Tr$ is the base temperature (100° C.).

Delignification Treatment

"Delignification treatment" refers here to a treatment that removes non-carbohydrate material such as lignin from lignocellulosic biomass. Delignification treatment also refers to a treatment that removes both non-carbohydrate and carbohydrate material as a mixture from lignocellulosic biomass.

Steam Explosion

In the context of the present invention the term "steam explosion" refers to a treatment, where the material is heated by a high pressure steam (at temperatures between 110° C. and 250° C., typically 140-230° C.) under a pressure with or without the addition of chemicals (such as acids) and the material is held at the temperature for a certain time after which the pressure is released causing an explosive decompression of the material. In this context, steam explosion is applied to lignocellulosic materials, and it typically results in a rupture of the lignocellulose fibers rigid structure, i.e. defibrillation of the cellulose fibre bundles.

Alkaline Delignification Agent

In the context of the present invention the term "alkaline delignification agent" refers to a chemical compound or a mixture of chemical compounds that when added to water give solutions with a hydrogen ion activity lower than that of pure water, i.e., a pH higher than 7.0. Alkaline delignification agent can be selected from a group of compounds comprising but not limited to hydroxides such as LiOH (lithium hydroxide), NaOH (sodium hydroxide), KOH (potassium hydroxide), $Ca(OH)_2$ (calcium hydroxide), $NH_4OH$ (ammonium hydroxide), or compounds that can form hydroxide ions in water such as $NH_3$ (ammonia) in liquid or gaseous state, carbonates such as $HCO_3^-$ (bicarbonate ion), $Li_2CO_3$ (lithium carbonate), $Na_2CO_3$ (sodium carbonate), $K_2CO_3$ (potassium carbonate), sulfides such as $Na_2S$ (sodium sulfide), and the corresponding hydrates.

Alkaline Delignification Treatment

In the context of the present invention the term "alkaline delignification treatment refers to treatment of lignocellulose performed in the presence of alkaline delignification agent, pH (starting pH) typically between 10 and 13. In alkaline delignification treatment hydroxen peroxide ($H_2O_2$) can be used in combination with alkaline delignification agent.

Enzymatic Hydrolysis

In the context of the present invention the term "enzymatic hydrolysis" refers to enzymatic treatment of the lignocellulosic material comprising cellulose and/or hemicellulose, oligosaccharides, where enzymes facilitates the hydrolysis of the cellulose and/or hemicellulose, oligosaccharides to obtain mono- and/or disaccharides. Typically the enzymatic hydrolysis treatment of the lignocellulosic material is conducted by subjecting the lignocellulosic material to a mixture of enzymes in the presence of water or a buffer. The mixture of enzymes typically consists of, but is not limited to 1,4-β-glucanases (endoglucanaces and exoglucanases, or endocellulases and exocellulases), 1,4-β-glucosidases (cellobiases) and hemicellulose-degrading enzymes (hemicellulases, xylanases, arabinases etc.).

Microbial Lipid or Lipid

In the context of the present invention "microbial lipid", "lipid" or "intracellular lipid" refers to a fatty substance, whose molecule generally contains, as a part, an aliphatic hydrocarbon chain, which dissolves in nonpolar organic solvents but is poorly soluble in water. Lipids are an essential group of large molecules in living cells. Lipids are, for example, fats, oils, waxes, wax esters, sterols, terpenoids, isoprenoids, carotenoids, polyhydroxyalkanoates, nucleic acids, fatty acids, fatty alcohols, fatty aldehydes, fatty acid esters, phospholipids, glycolipids, sphingolipids and acylglycerols, such as triacylglycerols, diacylglycerols, or monoacylglycerols. Preferred lipids in the present invention are fats, oils, waxes, acylglycerols and fatty acids and their derivatives, in particular triacylglycerols and wax esters. In the context of the present invention the lipids are synthesized by and accumulated in microbes (intracellular lipids). In another embodiment of the invention, lipids are synthetized by and excreted by microbes (extracellular lipids).

In connection of this invention single cell oil is used as synonym for lipids and fat.

The term "acyglycerol" refers to an ester of glycerol and fatty acids. Acylglycerols occur naturally as fats and fatty oils. Examples of acylglycerols include triacylglycerols (TAGs, triglycerides), diacylglycerols (diglycerides) and monoacylglycerols (monoglycerides).

Sugar

In the context of the present invention the term "sugar" refers here to oligomeric, dimeric and monomeric carbohydrates. Particularly, in this application the term sugar refers to water soluble oligomeric, dimeric and monomeric carbohydrates derived from lignocellulosic materials. By the term "polymeric sugars" is meant carbohydrates that are in polymeric form and not typically soluble in water.

Sugar Yield

In the context of the present invention the term "sugar yield" refers here to the yield of oligomeric, dimeric and monomeric carbohydrates from particular materials. Particularly, in this application the term sugar yield refers to the yield of water soluble oligomeric, dimeric and monomeric carbohydrates derived from lignocellulosic materials.

Single Cell Oil Production Process

"Single cell oil production process" refers here to a process, comprising steps of forming or allowing the growth of a lipid synthesizing microorganism and allowing the thus obtained organism mass to produce and/or store (accumulate) lipid, recovering the cells from the liquid phase, and extracting or recovering the lipids from the cells. In certain cases, single cell oil can be also extracellular such as excreted or liberated from cells in culture medium during or after cultivation.

Aerobic Cultivation

The term "aerobic cultivation" or "aerobic fermentation" refers to a cultivation where the microorganism utilizes oxygen as terminal electron acceptor for energy generation (i.e. microorganism uses aerobic respiration). Typically in bioreactors, aerobic cultivation is performed by adding oxygen or a gas mixture containing oxygen (typically air), i.e. bioreactor is aerated. When microorganisms uses aerobic respiration in cultivation, it can be referred as "cultivation under aerobic conditions". Typically this occurs in aerated bioreactors.

Oleaginous Microbe or Oil Producing Microorganism

The oleaginous microbe (also refer to as oil producing organisms) used in the present invention are selected from the group of bacteria, cyanobacteria, fungi such as yeasts and filamentous fungi, archaea or microalgae. The microorganisms can readily accumulate lipids or have been genetically modified to accumulate lipids or to improve accumulation of lipids.

Preferably organisms that are capable of utilizing C6 and C5 sugars are used. Preferably organisms are yeast, filamentous fungi or bacteria.

In the context of the present invention, the oleaginous microorganism (oleaginous microbe) refers to a microorganism which is capable of accumulating intercellular lipids such that the lipids mounts at least 15% (w/w) of the total biomass (per cell dry weight) of the microbe when it is cultivated under suitable conditions. In a preferred embodiment, the oleaginous microbe is capable of accumulating at least 20% (w/w) of the total biomass of the microbe (per cell dry weight).

Preferred microorganism strains for the purposes of the present invention include, but are not limited to, the species and genera listed below:

According to one embodiment of the invention, the microbe is an oleaginous microbe capable of utilizing sugars derived from lignocellulosic materials. Preferably, oleaginous organisms are capable of utilizing C6 sugars (six carbon sugars, such as glucose, mannose and galactose) and C5 sugars (such as xylose and arabinose) in lignocellulosic hydrolysates. According to one embodiment of the invention, the oleaginous organism is capable of utilizing polymeric or oligomeric carbohydrates in lignocellulose or fractions thereof.

Preferred (filamentous) fungal strains are from species from genera *Aspergillus* such as *Aspergillus oryzae*, *Mortierella* such as *Mortierella isabellina*, *Chaetomium*, *Claviceps*, *Cladosporidium*, *Cunninghamella*, *Emericella*, *Fusarium*, *Glomus*, *Mucor*, *Pseudozyma*, *Pythium*, *Rhizopus*, such as *Rhizopus oryzae*, *Tremella*, *Zygorhynchus*, *Humicola*, *Cladosporium*, *Malbranchea*, *Umbelopsis* such as *Umbelopsis isabellina* and *Ustilago*. Most preferred fungal species are from genera *Aspergillus* and/or *Mortierella*. Preferred fungi are those fungi capable of producing effectively lipids.

Preferred yeast strains are those belonging to species from genera, *Geotrichum*, *Deparyomyces*, *Pachysolen*, *Galactomyces*, *Hansenula*, *Leucosporidium*, *Sporobolomyces*, *Sporidiobolus*, *Waltomyces*, *Cryptococcus*, such as *Cryptococcus curvatus*, *Rhodosporidium*, such as *Rhodosporidium toruloides* or *Rhodosporidium fluviale*, *Rhodotorula*, such as *Rhodotorula glutinis*, *Yarrowia*, such as *Yarrowia lipolytica*, *Candida* such as *Candida curvata*, *Lipomyces* such as *Lipomyces starkeyi* and *Trichosporon* such as *Trichosporon cutaneum* or *Trichosporon pullulans*. Most preferred yeasts are from genera *Lipomyces*, *Rhodosporidium* and *Cryptococcus*. Preferred yeasts are those yeasts capable of producing effectively lipids.

Preferred bacteria are those belonging to the species from genera *Rhodococcus*, *Acinetobacter* and *Streptomyces*. Preferred bacteria are those bacteria capable of producing effectively lipids.

Most preferred algae are microalgae, such as microalgae species from genera comprising, *Brachiomonas*, *Crypthecodinium*, *Chlorella*, *Dunaliella*, *Hantzschia*, *Nannochloris*, *Nannochloropsis*, *Nitzschia*, *Prototheca*, *Scenedesmus*, *Schizochytrium*, *Traustrochytrium* and *Ulkenia*. Preferred microalgae are those microalgae capable of growing heterotrophically and producing effectively lipids. The organisms belonging to the genera *Schizochytrium*, *Thraustochytrium* and *Crypthecodinium* and *Ulkenia* are sometimes called as marine fungi.

According to another embodiment of the invention, the carbohydrates from lignocellulosic biomass are in mainly monomeric form and organisms not capable of utilizing oligomeric or polymeric carbohydrates are used for single cell oil production. Such oil producing organisms are selected from the group of bacteria, cyanobacteria, fungi such as yeasts and filamentous fungi, archaea or microalgae. The microorganisms can readily accumulate lipids or have been genetically modified to accumulate lipids or to improve accumulation of lipids.

Lipid Recovery

"Oil recovery" or "Lipid recovery" or "recovering lipid from an oleaginous microbe" refers to a process, in which the lipid (intracellular lipid) is recovered by mechanical, chemical, thermomechanical or autocatalytic methods or by a combination of these methods from the microorganism cells. Alternatively, "oil recovery" can mean the recovery of extracellularly produced lipids from the cultivation (fermentation) broth.

Lipid Containing Single-cell Mass

"Lipid-containing single-cell mass" stands for a single-cell mass and cellular mycelium with a lipid content of at least preferably at least 10%, preferably at least 15% (w/w) or more of dry matter of the microorganism biomass.

Residual Cell Mass

In the context of the present invention "residual cell mass" refers to a solid, semi-solid or flowing material fraction, which contains microorganisms treated for the recovery of intracellular lipids.

Biofuel

In the context of the present invention "biofuel" refers to solid, liquid or gaseous fuel mainly derived from biomass or biowaste and is different from fossil fuels, which are derived from the organic remains of prehistoric plants and animals.

According to EU directive 2003/30/EU "biodiesel" refers to a methyl-ester produced from vegetable oil or animal oil, of diesel quality to be used as biofuel. More broadly, biodiesel refers to long-chain alkyl esters, such as methyl, ethyl or propyl-esters, from vegetable oil or animal oil of diesel quality. Biodiesel can also be produced from microorganism lipids, whereby microorganism lipid can originate from a bacterium, a fungus (yeast or a mold), an algae or another microorganism.

Renewable Diesel

"Renewable diesel" refers to a fuel which is produced by a hydrogen treatment of lipids of an animal, vegetable or microorganism origin, or their mixtures, whereby microorganism lipid can originate from a bacterium, a fungus (a yeast or a filamentous fungus), an algae or another microorganism. Renewable diesel can be produced also from waxes derived from biomass by gasification and Fischer-Tropsch synthesis. Optionally, in addition to hydrogen treatment, isomerization or other processing steps can be performed. Renewable diesel process can also be used to produce jet fuel and/or gasoline. The production of renewable diesel has been described in patent publications EP 1396531, EP1398364, EP 1741767 and EP1741768.

Biodiesel or renewable diesel may be blended with fossil fuels. Suitable additives, such as preservatives and antioxidants may be added to the fuel product.

Lubricant

"Lubricant" refers to a substance, such as grease, lipid or oil that reduces friction when applied as a surface coating to moving parts. Two other main functions of a lubricant are heat removal and to dissolve impurities. Applications of lubricants include, but are not limited to uses in internal combustion engines as engine oils, additives in fuels, in oil-driven devices such as pumps and hydraulic equipment, or in different types of bearings. Typically lubricants contain 75-100% base oil and the rest is additives. Suitable additives are for example detergents, storage stabilizers, antioxidants, corrosion inhibitors, dehazers, demulsifiers, antifoaming agents, co-solvents, and lubricity additives (see for example U.S. Pat. No. 7,691,792). Base oil for lubricant can originate from mineral oil, vegetable oil, animal oil or from a bacterium, fungi (yeast or a filamentous fungus), an algae or another microorganism. Base oil can also originate from waxes derived from biomass by gasification and Fischer-Tropsch synthesis. Viscosity index is used to characterise base oil. Typically high viscosity index is preferred.

The lipids produced according with the method described in this invention can be used as feedstock for the production of biodiesel, renewable diesel, jet fuel or gasoline. Biodiesel consists of fatty acid methyl esters, and is typically produced by transesterification. In transesterification, the acylglycerols are converted to long-chain fatty acid alkyl (methyl, ethyl or propyl) esters. Renewable diesel refers to fuel which is produced by hydrogen treatment (hydrogen deoxygenation, hydrogenation or hydroprocessing) of lipids. In hydrogen treatment, acylglycerols are converted to corresponding alkanes (paraffins). The alkanes (paraffins) can be further modified by isomerization or by other process alternatives. Renewable diesel process can also be used to produce jet fuel and/or gasoline. In addition, cracking of lipids can be performed to produce biofuels. Further, lipids can be used as biofuels directly in certain applications.

Lipids produced with the method can also be used as base oils for lubricants (lubrication oils) or as a starting material for production of base oils for lubricants Dry Matter "DM" or "dry weight" refers here to dry matter and is a measurement of the mass of a material when it has been subjected to a treatment that essentially removes water from the material (i.e. material is completely dried).

Consistency

"Consistency" refers here to the ratio of dry weight of solids to total weight of suspension.

Method for Fractionation of a Lignocellulosic Material

One object of the present invention is to provide a fractionation method, which has an improved cost-efficiency of the aerobic fermentation process due to the low amount of inert material (lignin) and inhibitor compounds in the sugar fraction used in aerobic fermentation.

The inventors have surprisingly discovered that the alkaline delignification can be effectively done without the excessive application of alkaline delignification agent if the lignocellulosic material is subject to a hydrothermal treatment, such as autohydrolysis, prior to the alkaline delignification. One advantage of is decreased consumption of alkaline agent in delignification and subsequently decrease consumption of acid in the precipitation of dissolved lignin and in the pH adjustment prior to enzymatic hydrolysis.

In a first aspect of the present invention relates to a method for fractionation of a lignocellulosic material, the method comprising a) Subjecting the lignocellulosic material to a treatment wherein hemicellulose is at least partially removed from the lignocellulosic material to produce a mixture comprising a first liquid phase and a first solid phase, b) Separating the first solid phase from the first liquid phase, c) Subjecting the first solid phase to a delignification treatment in the presence of alkaline delignification agent to produce a mixture comprising a second solid phase and a second liquid phase containing solubilized lignin, d) Separating the second solid phase from the second liquid phase, e) Subjecting the second solid phase to an enzymatic hydrolysis treatment in the presence of enzymes capable of hydrolysing the hemicellulose and cellulose fractions of the second solid phase to produce a mixture comprising a third liquid phase in the form of an enzymatic hydrolysate and a third solid phase.

In a further step, the mixture of the third liquid phase comprising the cellulosic carbohydrates may be separated from the third solid phase comprising lignin.

Figure 2:
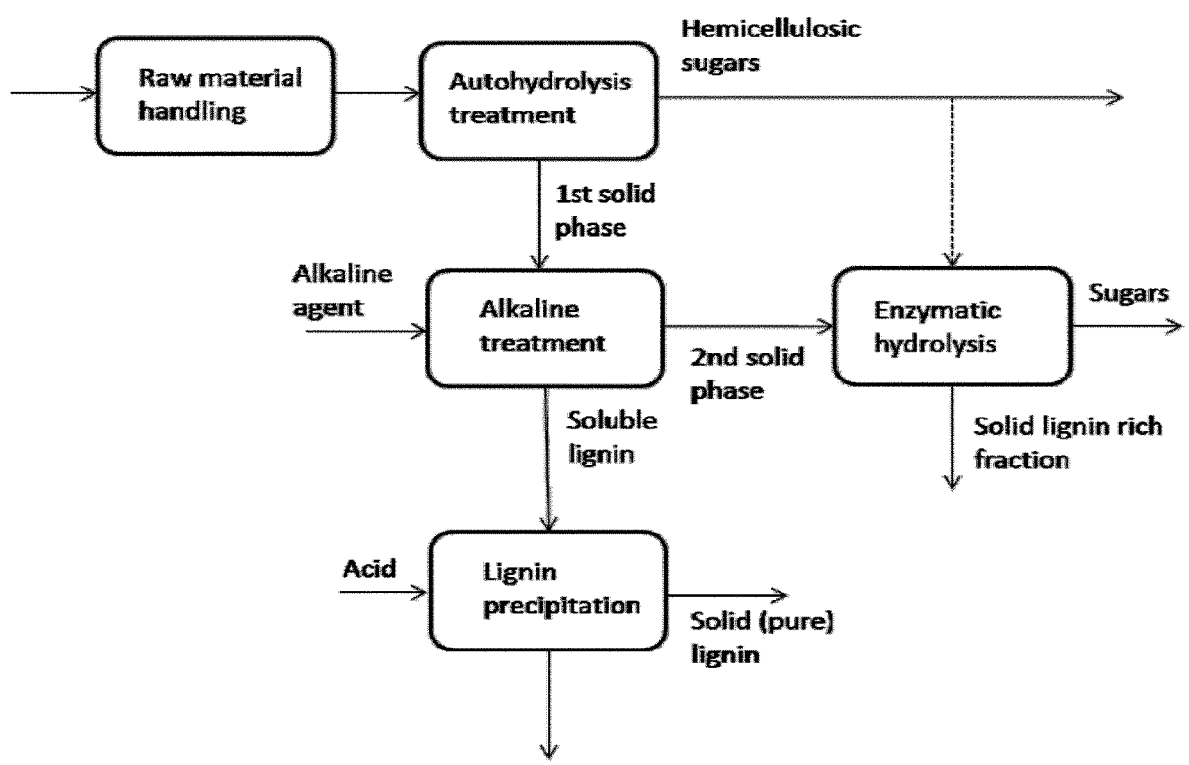
Figure 3:
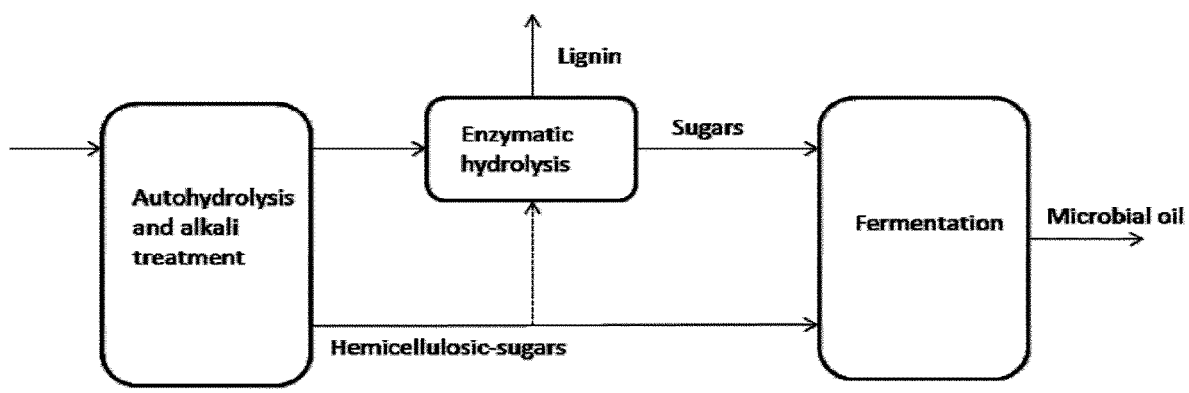

An embodiment of the method of the invention is schematically illustrated in FIG. 1. Another embodiment of the method of the invention is schematically illustrated in FIG. 2. The embodiment shown in FIG. 2 includes a method of precipitation the soluble lignin (first liquid phase) obtained from the alkaline treatment using acid.

Step of Partially Removing the Hemicellulosic Sugars from the Lignocellulosic Material In step a) of the method of fractionation of the lignocellulosic material, the lignocellulosic material is subjected to a treatment wherein hemicellulose is at least partially removed from the lignocellulosic material to produce a first liquid phase and a first solid phase. In step a) of the fractionation method, the hemicelluloses are at least partly dissolved and separated in a liquid phase (referred to as the first liquid phase)

The first liquid phase can be obtained directly from the treatment of lignocellulosic where at least part of the hemicellulose becomes soluble in water (i.e. the treatment results in a liquid phase). Alternatively, the treatment does not result in a liquid phase (i.e. is carried out in such high consistency that liquid phase does not exist) and the first liquid phase is obtained by washing the solid material that has undergone a treatment where at least part of the hemicellulose becomes soluble in water. Alternatively, the first liquid phase can be produced directly from the treatment and additionally the solid phase is further washed and resulting liquid combined with the first liquid phase.

In another embodiment of the present invention, the hemicellulose is at least partially removed from the lignocellulosic material by hydrothermal treatment. In a second embodiment, the hydrothermal treatment is conducted at a temperature of between 100 and 250° C., preferably between 140 and 240° C., and most preferably between 140 and 200° C. The intensification of the hydrothermal treatment may be expressed in terms of severity, the term which is defined herein. In a preferred embodiment, the hydrothermal treatment is conducted in a conditions corresponding to severity of between 2.0 and 4.5, preferably between 3.0 and 4.1, most preferably between 3.5 and 4.0.

In one embodiment of the present invention, the hemicellulose is at least partially removed from the lignocellulosic material by autohydrolysis treatment. The autohydrolysis is typically performed at 5-60% dry matter content, at temperatures between 140 and 240 C for 1-120 min without addition of acidic compounds resulting in dissolving of 5- to 40% of dry matter content in lignocellulosic material including hemicellulosic carbohydrates. Typically autohydrolysis dissolves from 30 to 100% of hemicellulosic cerbohydrates from lignocellulosic material, preferably more >50%, more preferably >70%, more preferably >80%, even more preferably >90%. The dissolved hemicellulose carbohydrates are at least partly in oligomeric form. More typically, the autohydrolysis is performed at 10-50% dry matter content at 160-220 C, depending on the lignocellulosic raw material. After autohydrolysis, the solid and liquid phases are separated by any method, such as filtration, e.g. pressure filtration, or by a screw press. The solid fraction may be washed to remove dissolved hemicellulose from solid phase.

According to another embodiment of the invention, the lignocellulosic material is subjected to a steam or steam explosion with or without addition of acidic compounds, in general at temperatures between 110 and 250° C., more typically at temperatures between 140 and 230° C. The treatment results in a dissolving of hemicellulosic carbohydrates. Optionally, the solid material from steam explosion is washed to recover dissolved hemicellulosic carbohydrates.

Figure 4:
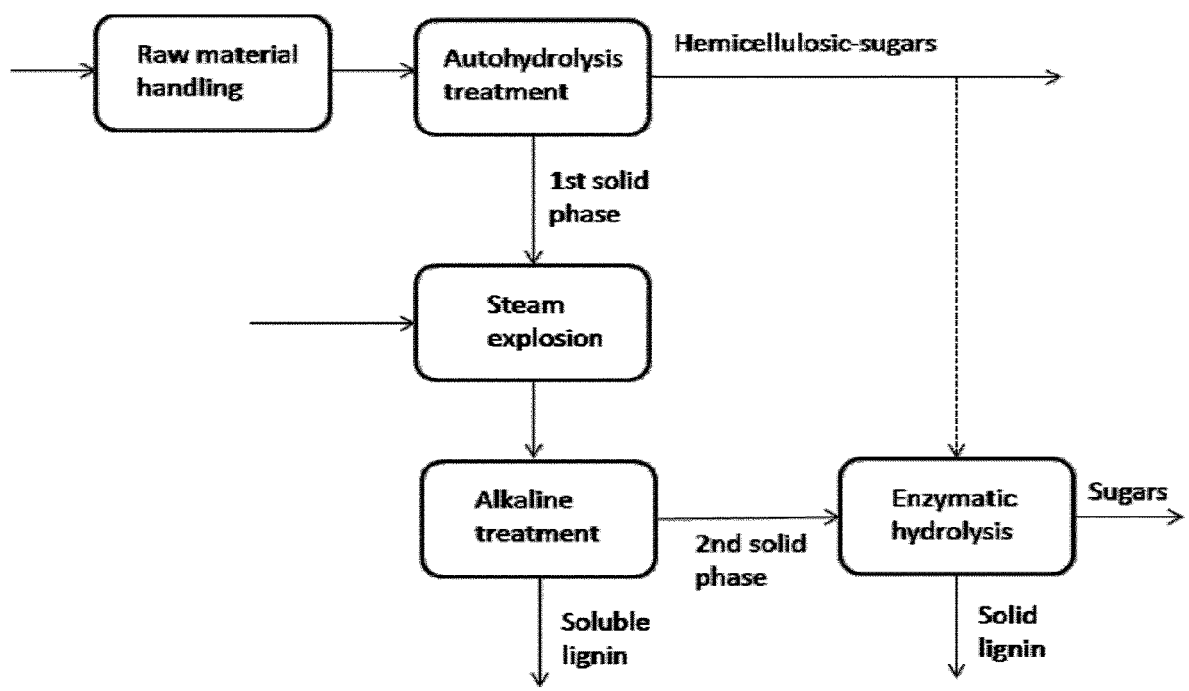

In one embodiment of the present invention, the lignocellulosic material is first subjected to hydrothermal treatment followed by a step of steam explosion (exemplified in FIG. 4). In another embodiment, the first solid phase is subjected to a steam explosion before the delignification treatment in the presence of the alkaline delignification agent According to the invention, the lignocellulose treatment according to step a) (where hemicellulosic sugars become at least partly dissolved) enables efficient recovery of hemicellulosic sugars for microbial cultivation such as production of single cell oil.

Alkaline Delignification Step

In step c) of the method of fractionation of the lignocellulosic material, the first solid phase (comprising lignocellulosic material from which the hemicellulosic material has been partly removed) is subjected to a step of alkaline delignification, wherein at least part of lignin is solubilised. The alkaline delignification is performed by subjecting the lignocellulosic material from which the hemicellulosic material has been partly removed to an alkaline delignification agent.

The alkali treatment is typically conducted by preparing a suspension comprising autohydrolysed lignocellulose material, aqueous liquid, and one or more alkaline agents, or mixtures thereof to give pH of the suspension above pH 7. Preferably alkaline chemical is added to an amount to give pH of suspension between 10 and 13 in the beginning of the treatment. Typically, the pH decreases during the alkaline treatment.

The alkaline suspension is kept at temperatures where suspension contains at least one liquid phase. The incubation is not limited to any certain temperature but can be conducted at wide temperature range isothermally or non-isothermally. Incubation is preferably carried out at temperatures from 25° C. preferably between 30 and 160° C.

Agitation is optionally conducted to increase efficacy of heat transfer during incubation. Treatment time is selected according to intended degree of dissolution material. Preferably treatment time is from half an hour to twenty hours.

After reaction time the second liquid phase and second solid phase are separated by using any method such as but not limited to filtration, e.g. pressure filtration or screw press. The second solid phase is used for enzymatic hydrolysis to release sugars for further use such as microbial oil production. The second liquid phase can be treated to precipitate lignin, such as by acid treatment and precipitated lignin can be separated by any method.

In one embodiment of the present invention, the alkaline delignification agent is selected from a group consisting of sodium hydroxides, sodium carbonates, potassium hydroxides, potassium carbonates, calcium hydroxides, calcium carbonates, lithium hydroxide, lithium carbonate, ammonium hydroxide, ammonia, sodium sulphide, and the corresponding hydrates. In a preferred embodiment, the alkaline delignification agent is sodium hydroxide or sodium carbonate.

As mentioned above, the inventors have surprisingly discovered that the alkaline delignification can be effectively done without the excessive application of alkaline delignification agent if the lignocellulosic material is subject to a hydrothermal treatment, such as autohydrolysis, prior to the alkaline delignification. The hydrothermal treatment results in decreased acidity of solid fraction (comprising cellulose, lignin and residual hemicellulose). Therefore, in alkaline treatment less alkaline agent is needed compared to the situation when hydrothermal treatment is not performed. Therefore, alkaline treatment after hydrothermal treatment can be performed at lower pH compared to the situation without autohydrolysis. Thus, hydrothermal treatment is beneficial prior to alkaline treatment of lignocellulosic material. One advantage of applying lower amounts of the alkaline delignification agent is that less sugar is lost in the alkaline delignification step compared to a similar treatment conducted in the presence of high amounts of the alkaline delignification agent.

Accordingly, in a preferred embodiment of the present invention, the concentration of delignification agent is from 0.1 to 10 wt %, more preferably 0.1-4 wt-% based on the amount of dry matter in first solid phase. In a further embodiment, the alkaline delignification agent is added to the first solid phase to obtain a suspension having a pH of above 7, preferably between 10 and 13.

In a further embodiment, the delignification treatment is conducted at a temperature of above 25, preferably between 30 and 160° C.

According to yet another embodiment of the invention, the delignification of lignocellulosic material is performed with ammonium as delignification chemical. According to one embodiment of the invention, ammonium fibre expansion (AFEX) or ammonia recycle percolation is used with temperature between 60 C and 220° C.

According to the invention, the lignocellulose treatment according to step c) the alkaline delignification enables efficient enzymatic hydrolysis and efficient recovery of cellulosic sugars for microbial cultivation such as production of single cell oil.

Enzymatic Hydrolysis of Alkaline Delignification Product

In step e) of the method of fractionation of the lignocellulosic material, the second solid phase obtained from the alkaline delignification step is subjected to enzymatic hydrolysis Enzymatic Hydrolysis Enzymatic hydrolysis consists of incubation of pretreated straw or other substrate or raw material, with a mixture of enzymes, which typically consists of, but is not limited to 1,4-β-glucanases (endoglucanaces and exoglucanases, or endocellulases and exocellulases), 1,4-β-glucosidases (cellobiases) and hemicellulose-degrading enzymes (hemicellulases, xylanases, arabinases etc.). The enzymes may or may not be commercial enzyme products. The pretreated straw is mixed with water or buffer solution and the enzyme mixture at appropriate proportions. Additives, such as polyethylene glycol, detergents or other surface active agents, or proteins may or may not be added to the reaction. Any proportion of solids in the suspension (or "consistency") may be used, preferably 10-35%, or particularly 15-25%. The pH of the slurry is adjusted according to the optimal conditions for the used enzyme mixture. The pH adjustment is performed before and/or during the addition of enzyme by adding acid or base at a suitable concentration, for example $H_2SO_4$, HCl, $HNO_3$, NaOH, $NH_3$ or other acid or base. Further pH adjustment may or may not be performed after the addition of enzymes and during hydrolysis.

A constant temperature is maintained during the hydrolysis, according to the optimal conditions of the enzyme mixture, often 40-60° C., or particularly 50° C. The pre-treated straw, water and/or buffer solution and other constituents of the hydrolysis suspension may or may not be preheated to the reaction temperature before they are added to the suspension. The suspension is agitated during the reaction by stirring, shaking, free falling or by other means of agitation.

In one embodiment of the present invention, the enzymatic hydrolysis treatment of the lignocellulosic material is conducted by subjecting the lignocellulosic material to a mixture of enzymes in the presence of water or a buffer. The mixture of enzymes typically consists of, but is not limited to 1,4-β-glucanases (endoglucanaces and exoglucanases, or endocellulases and exocellulases), 1,4-β-glucosidases (cellobiases) and hemicellulose-degrading enzymes (hemicellulases, xylanases, arabinases etc.).

By the subjecting the second solid phase obtained from the alkaline delignification step to an enzymatic hydrolysis step, sugars are dissolved from the solid material. A solid-liquid separation by any method is performed after the enzymatic treatment forming a third liquid phase containing the sugars dissolved during the hydrolysis and a third solid phase comprising lignin and residual polymeric sugars (residual fibre). The third liquid phase is also referred to as the enzymatic hydrolysate, which may be used for the production of microbial lipids.

Part of the hemi-cellulosic sugars separated from the material in step a) (for example by hydrothermal treatment or autohydrolysis) may be introduced into the system and subjected to enzymatic hydrolysis together with the solid phase material obtained from the delignification step (second solid phase).

Thus at least part of the first liquid phase may be added to and mixed with the second solid phase before this mixture is subjecting to the enzymatic hydrolysis treatment of step e). Thus, in one embodiment of the invention, at least part of the first liquid phase is combined with the second solid phase and subjected to enzymatic hydrolysis treatment.

Alternatively, enzymatic hydrolysis of the first liquid phase is performed separately from the second solid phase.

According to the invention, it was surprisingly discovered that the lignocellulose treatment method which includes the sequential steps of subjecting the lignocellulose to a treatment by which hemicellulosic sugars become at least partly dissolved (such as autohydrolysis) and then subjecting the solid phase obtained from this treatment to a step of alkaline delignification (such as treatment with NaOH) a higher overall (total) sugar yield in obtained. The high overall sugar yield is beneficial for cost-efficiency of microbial processes such as production of single cell oil.

In one embodiment of the present invention, the enzymatic hydrolysis is conducted as a batch hydrolysis.

Batch Hydrolysis

Batch hydrolysis refers to a hydrolysis reaction, where the reaction constituents are mixed to form a suspension or a slurry or a paste, and incubated for an appropriate period of time, after which the solids are separated by filtration, centrifugation or other means of separation and a liquid stream of soluble sugars, including glucose, xylose arabinose, galactose, mannose and others, and oligomers thereof, is acquired. Reaction constituents or other substances may or may not be added during the reaction. However, no liquid stream is separated from the slurry before the end of the reaction.

A batch reaction may also be performed as a continuous process. In a continuous batch hydrolysis, a constant stream of fractionated (pre-treated) lignocellulosic material, liquid, enzymes, pH-adjustment agents and other reaction constituents is fed to the reactor while simultaneously a constant stream of slurry is removed from the reactor, from which the liquid stream is separated. In a continuous batch hydrolysis, the reactor may or may not be subdivided into two or more reactors in series, through which the slurry flows constantly, particularly in order to improve the retention time distribution of the raw material. Conceptually, the solid material is separated from liquid only after the reaction and no separation takes place during the reaction. Therefore no separation takes place for the outflowing slurry from other reactors except the slurry from the last reactor and, accordingly, no other separate liquid stream is removed from the slurry, than the liquid stream from the separation of the final outflowing slurry. However, additional feed of reaction constituents may take place at any point of the process. If separation of liquid takes place between two reactors, the reactors should be defined as separate reaction steps and the hydrolysis process should be defined as a sequential (stepwise) hydrolysis.

Figure 5:
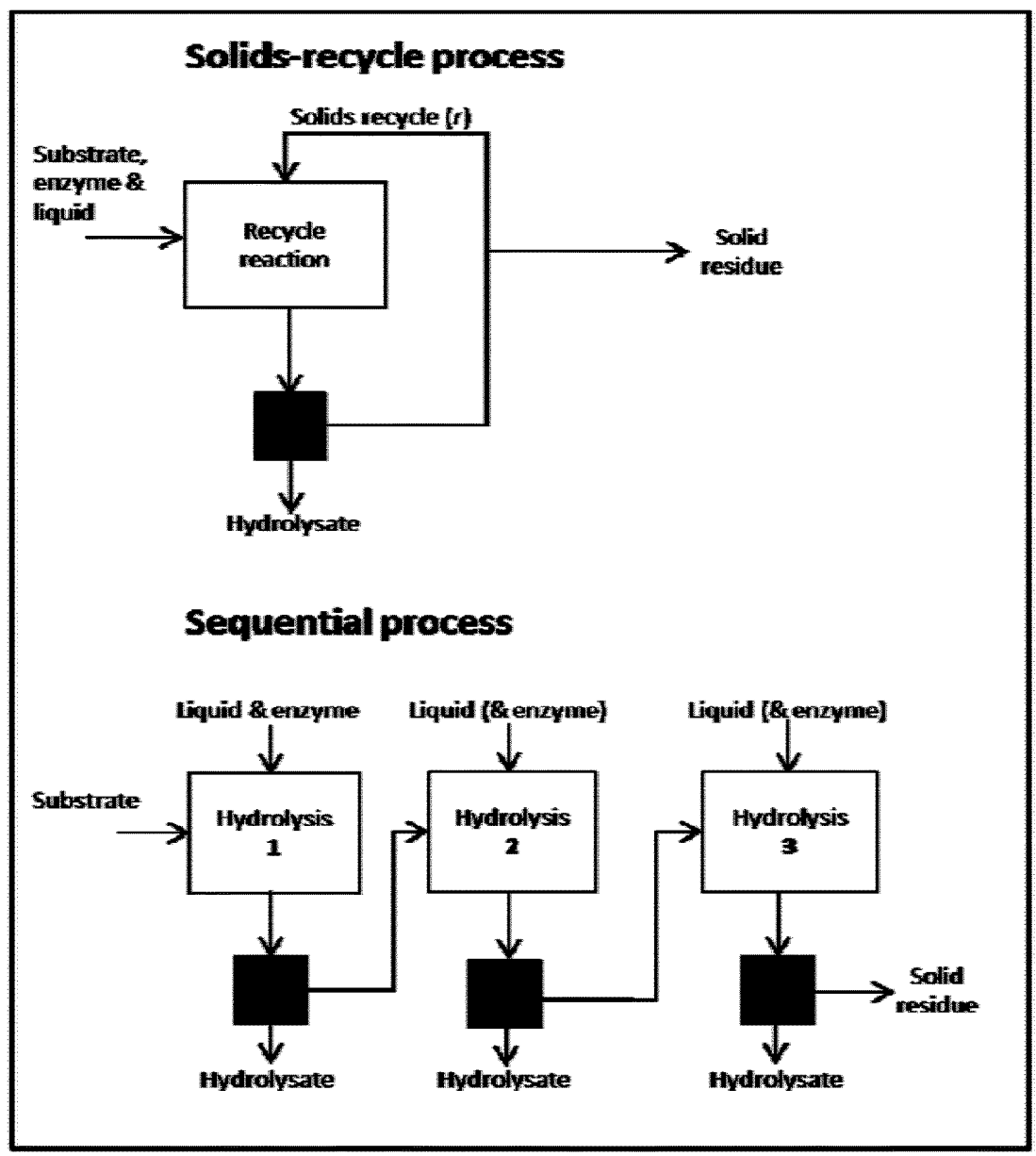
FIG. 5 presents process scheme for the enzymatic hydrolysis according to the embodiments of the invention.

In a second embodiment, the enzymatic hydrolysis is conducted as a sequential hydrolysis, such as illustrated in FIG. 5.

Sequential Hydrolysis

Sequential hydrolysis, also known as stepwise hydrolysis, or two-stage, three-stage or multi-stage hydrolysis, etc., consists of a sequence of batch reactions in series, where between the batch reactions, a liquid stream is separated from the slurry and the concentrated solid stream is fed to the next batch reaction and mixed with fresh water and/or buffer solution. Addition of fresh enzymes and other reaction constituents may or may not take place into the second, third, or latter reaction. The reaction time may be equal or different in the subsequent reaction steps. The process flow of a sequential reaction is presented in FIG. 5.

Similarly as described for batch reactions, the sequential hydrolysis may be performed as a continuous process and the singe reaction steps of the sequential hydrolysis may be subdivided into separate reactors in series, through which the slurry flows constantly. Separation of liquid and addition of fresh liquid may or may not take place between the reactors. Conceptually, if liquid is separated and the liquid is or is not replaced by fresh liquid between two reactors, the reactors should be defined as separate reaction steps.

In yet a further embodiment, the enzymatic hydrolysis is conducted as a solid recycle hydrolysis, such as illustrated in FIG. 5.

Recycling of residual solids in enzymatic hydrolysis (or "solids-recycling")

A hydrolysis process with recycling of the residual solids, or "solids-recycling", includes a hydrolysis reaction, after which a liquid stream is separated from the slurry and a proportion of the concentrated solid stream is recycled back to the same reactor (FIG. 5). The proportion of recycled residual solids is called the recycle rate and denoted by r in FIG. 5 and in Eq. 2 & 3. At a constant raw material feed rate, the solids-recycling extends the reaction time of the solid material according to a geometrical series, presented in Eq. 2, where to is the average reaction time of the solids after n subsequent recycle reactions, t0 is the reaction time of a single reaction, or the retention time of the slurry in the reactor, and r is the recycle rate. Eventually, a recycle process at constant feed and recycle rates and a constant retention time will reach a steady state, at which the average reaction time of the solid material may be calculated from Eq. 3.

$$t_n = \sum_{i=0}^{n-1} t_0 r^i = t_0 \frac{1-r^n}{1-r} \quad (2)$$

$$t_{Std} = \sum_{i=0}^{\infty} t_0 r^i = \frac{t_0}{1-r} \quad (3)$$

For example, 50% recycle rate in a 24 h reaction, the average reaction time of the solids will be 48 h at steady state.

The recycle reaction may be performed as a batch reaction, after which solids-recycling takes place, or as a continuous process, where the process constituents are constantly fed to the reactor, a constant outflow of slurry takes place and the outflowing slurry is separated to a liquid and a concentrated residual solid stream and a constant flow of residual solids is recycled back to the reactor. The recycle reaction may or may not be subdivided into separate reactors in series in order to improve the residence time distribution and separation of liquid from or after these reactors and additional feed of process constituents into these reactors may or may not take place. Additional sequential reaction steps may or may not be included after or before or during the solids-recycling reaction.

The liquid enzymatic hydrolysate obtained in step e) may be subject to a step of concentrating the hydrolysate, such as by evaporation, to obtain a concentrated hydrolysate. Thus, in one embodiment the method according of the invention includes further comprising a step of concentrating the third liquid phase. Preferably, the concentrating of third liquid phase is done by evaporation.

Liquid Enzymatic Hydrolysate (Third Liquid Phase)

The liquid phase comprising the cellulosic sugars may be used in the preparation of a cultivation medium, such as cultivation medium for use in a method for producing microbial lipids as described herein.

Accordingly, a second aspect of the present invention relates to a liquid phase in the form of an enzymatic hydrolysate obtainable by the method of the present invention (the third liquid phase).

Alternatively, the liquid phase the enzymatic hydrolysate may be concentrated to obtained liquor having a higher concentration of sugars. Thus, a further aspect of the present invention provides a concentrated sugar hydrolysate obtainable by the method of the present invention.

The enzymatic hydroysate from first liquid phase (comprising hemicellulosic sugar monomers) and enzymatic hydrolysate, the third liquid phase (comprising cellulosic sugars) can be used in cultivation broth alone or mixed together as carbon sources for production of single cell oil.

Precipitated Lignin Fraction (Obtained from the Second Liquid Phase)

The precipitated lignin may be obtained by treating the second liquid phase comprising the soluble lignin with acid and separated the precipitated pure lignin as illustrated in FIG. 2.

Accordingly, in one embodiment of the present invention the method includes a further step of precipitating lignin from the second liquid phase by lowering the pH of the solution and the precipitated lignin is recovered by any suitable separation method such as filtration.

The inventors of the present invention have discovered that the lignin fraction obtained by the method of the present invention is particular pure (see Example 9).

Thus, a fourth aspect relates to a precipitated lignin fraction obtainable by the method of the invention.

The separated lignin fraction can be used for value added applications compared to combustion value, such as in resin (e.g. phenolic resin applications) or polymer applications. Optionally, the separated lignin fraction is washed and/or further treated to purify it prior to use in value added applications.

Method for Production of Microbial Lipid

A further aspect of the present invention relates to a method for production of microbial lipid, the method comprising
 (i) providing a cultivation medium comprising the third liquid phase obtained by method for fractionation of a lignocellulosic material (comprising mainly cellulosic carbohydrates) or the concentrated sugar hydrolysate of the present invention,
 (ii) providing a fermentation broth by inoculating the cultivation medium with an oleaginous microbe,
 (iii) incubating said medium inoculated with said oleaginous microbe allowing lipid to accumulate,
 (ii) recovering the lipid from said oleaginous microbe.

The method of the invention is also referred to as a single cell oil production process. The method of the present invention may be part of process for productions of biofuels as described herein, where the oil or at least part of the oil provided in the form of microbial oil by the method described herein.

According to preferred embodiment of the invention the cultivation medium comprises lignocellulosic sugars derived from cellulose and/or hemicellulose. According to the invention, both hemicellulose and/or cellulose fractions of lignocellulosic biomass are used as raw materials for microbial oil production (single cell oil) in the same process (bioreactor system). The process uses preferably oleaginous microbe that are capable of utilizing both C6 (e.g glucose, mannose, galactose) and C5 (e.g. xylose, arabinose) sugars.

According to another embodiment of the invention, the cultivation medium comprises hemicellulosic sugars derived from lignocellulose. According to yet another embodiment of the invention, the hemicellulosic sugars are at least partly in oligomeric form when fed to a single cell oil production process.

In a preferred embodiment of the present invention the method for production of microbial lipid according to the preceding claim, the method comprises the steps of
 a) Subjecting the lignocellulosic material to a treatment wherein hemicellulose is at least partially removed from the lignocellulosic material to produce a mixture comprising a first liquid phase and a first solid phase,
 b) Separating the first solid phase from the first liquid phase, c) Subjecting the first solid phase to a delignification treatment in the presence of alkaline delignification agent to produce a mixture comprising a second solid phase and a second liquid phase containing solubilized lignin, d) Separating the second solid phase from the second liquid phase, e) Subjecting the second solid phase to an enzymatic hydrolysis treatment to hydrolyse the hemicellulose and cellulose fractions of the second solid phase to produce a mixture comprising a third liquid phase of enzymatic hydrolysate and a third solid phase.

f) separating the third liquid phase and the third solid phase, (i) providing a cultivation medium comprising the third liquid phase of enzymatic hydrosylate of step f) and optionally the first liquid phase or enzymatic hydroysate thereof, (ii) providing a fermentation broth by inoculating the cultivation medium with an oleaginous microbe, (iii) incubating said medium inoculated with said oleaginous microbe allowing lipid to accumulate (iv) recovering the lipid from said oleaginous microbe.

The microbes used by the method for producing microbial lipids are oleaginous microbes. The oleaginous microbes (as described herein) are capable of accumulating intercellular lipids such that the lipids mounts at least 15% (w/w) of the total biomass (per cell dry weight) of the microbe when it is cultivated under suitable conditions. In a preferred embodiment, the oleaginous microbe is capable of accumulating at least 20% (w/w) of the total biomass of the microbe (per cell dry weight). In one embodiment of the present invention, oleaginous microbe used for the production of lipids is selected from a group comprising yeast and filamentous fungi. Preferably, a method for production of microbial lipid is carried out under aerobic condition. Thus, in one embodiment of the present invention, the incubation in step (iii) is conducted as aerobic cultivation, such as described herein.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

The term "comprising", "comprise" and "comprises" herein are intended by the applicant to be optionally substituted with the terms "consisting of", "consist of" or "consists of", respectively, in every instance.

Items

In the following the invention is described by way of non-limiting items

Item 1. Method for fractionation of a lignocellulosic material, the method comprising a) Subjecting the lignocellulosic material to a treatment wherein hemicellulose is at least partially removed from the lignocellulosic material to produce a mixture comprising a first liquid phase and a first solid phase, b) Separating the first solid phase from the first liquid phase, c) Subjecting the first solid phase to a delignification treatment in the presence of alkaline delignification agent to produce mixture comprising a second solid phase and a second liquid phase containing solubilized lignin, d) Separating the second solid phase from the second liquid phase, e) Subjecting the second solid phase to an enzymatic hydrolysis treatment in the presence of enzymes capable of hydrolysing the hemicellulose and cellulose fractions of the second solid phase to produce a mixture comprising a third liquid phase and a third solid phase.

Item 2. The method according to item 1, wherein at least part of the first liquid phase is combined with the second solid phase and subjected to enzymatic hydrolysis treatment.

Item 3. The method of item 1, wherein the hemicellulose is at least partially removed from the lignocellulosic material by hydrothermal treatment.

Item 4. The method according to item 1, wherein the hemicellulose is at least partially removed from the lignocellulosic material by autohydrolysis treatment.

Item 5. The method according to any one of the preceding items, wherein the alkaline delignification agent is selected from a group consisting of sodium hydroxide, sodium carbonate, potassium hydroxide, potassium carbonate, calcium hydroxide, calcium carbonate, lithium hydroxide, lithium carbonate, ammonium hydroxide, ammonia, sodium sulphide, and the corresponding hydrates.

Item 6. The method according to any one of the preceding items, wherein the concentration of delignification agent is from 0.1 to 10 wt %, preferably 0.1 to 4 wt-% based on the amount of dry matter in first solid phase.

Item 7. The method according to any one of the preceding items, wherein the alkaline delignification agent is added to the first solid phase to obtain a suspension having a pH of above 7, preferably between 10 and 13.

Item 8. The method according to any one of the preceding items, wherein the delignification treatment is conducted at a temperature of above 25, preferably between 30 and 160° C.

Item 9. The method according to any one of the preceding items, wherein the hydrothermal treatment is conducted at a temperature of between 100 and 250° C., preferably between 140 and 240° C., and most preferably between 140 and 200° C.

Item 10. The method according to any one of the preceding items, wherein the hydrothermal treatment is conducted in a conditions corresponding to severity of between 2.0 and 4.5, more preferably between 3.0 and 4.1, and most preferably between 3.5 and 4.0.

Item 11. The method according to any of one of the preceding items, wherein the first solid phase is subjected to a steam explosion before said delignification treatment.

Item 12. The method according to any of one of the preceding items, wherein the enzymatic hydrolysis is conducted as a batch hydrolysis.

Item 13. The method according to any of one of the preceding items, wherein the enzymatic hydrolysis is conducted as a sequential hydrolysis.

Item 14. The method according to any of one of the preceding claims, wherein the enzymatic hydrolysis is conducted as a solid recycle hydrolysis.

Item 15. The method according to any of one of the preceding items, wherein the lignin is precipitated from the second liquid phase by lowering the pH of the solution and the precipitated lignin is recovered by any suitable separation method such as filtration.

Item 16. The method according to any of one of the preceding items further comprising a step of concentrating the third liquid phase.

Item 17. A liquid phase in the form of an enzymatic hydrolysate obtainable by the method according to any one of the preceding items.

Item 18. A concentrated sugar hydrolysate obtainable by the method according to items 16.

Item 19. A precipitated lignin fraction obtainable by the method of items 15.

Item 20. A method for production of microbial lipid, the method comprising
  (i) providing a cultivation medium comprising the third liquid phase of item 17 or the concentrated sugar hydrolysate of item 18,
  (ii) providing a fermentation broth by inoculating the cultivation medium with an oleaginous microbe,
  (iii) incubating said medium inoculated with said oleaginous microbe allowing lipid to accumulate,
  (iv) recovering the lipid from said oleaginous microbe.

Item 21. The method for production of microbial lipid according to the preceding item, the method comprising
  a) subjecting the lignocellulosic material to a treatment wherein hemicellulose is at least partially removed from the lignocellulosic material to produce a mixture comprising a first liquid phase and a first solid phase,
  b) separating the first solid phase from the first liquid phase,
  c) subjecting the first solid phase to a delignification treatment in the presence of alkaline delignification agent to produce mixture comprising a second solid phase and a second liquid phase containing solubilized lignin,
  d) separating the second solid phase from the second liquid phase,
  e) subjecting the second solid phase to an enzymatic hydrolysis treatment to hydrolyse the hemicellulose and cellulose fractions of the second solid phase to produce a mixture comprising a third liquid phase of enzymatic hydrolysate and a third solid phase.
  f) Separating the third liquid phase of an enzymatic hydrolysate from the third solid phase.
  (i) providing a cultivation medium comprising the third liquid phase of enzymatic hydrosylate of step f),
  (ii) providing a fermentation broth by inoculating the cultivation medium with an oleaginous microbe,
  (iii) incubating said medium inoculated with said oleaginous microbe allowing lipid to accumulate
  (iv) recovering the lipid from said oleaginous microbe.

Item 22. The method according to any one of items 20 or 21, wherein the microorganism used for the production of lipids is selected from a group comprising yeast and filamentous fungi.

EXAMPLES

The invention is illustrated by the following non-limiting examples. The invention can be applied to other lignocellulosic raw materials than those illustrated in examples. It should be understood that the embodiments given in the description above and in the examples are for illustrative purposes only, and that various changes and modifications are possible within the scope of invention.

Example 1

Autohydrolysis (with Pre-adjusted pH) of Wheat Straw

A suspension was prepared by mixing 20 g wheat straw previously milled to pass a 1 mm screen and 180 g water. The suspension was adjusted with acetic acid to pH 4.5. The suspension was transferred into an autoclave reactor that was then non-isothermally heated up with a heating jacket to temperature between 170° C. and 200° C. with continuous stirring. The temperature data during the heating was recorded and used to calculate autohydrolysis severity (Eq. 1). The reactor was cooled to approximately 50 C, and the suspension was manually recovered for filtration. The liquid fraction was separated from the solid fraction and furfural and hydroxymethyl furfural (HMF) in the liquid fraction were measured using HPLC. Total concentration of sugar (g/l) in the liquid fraction was determined after dilute acid hydrolysis that converts oligomeric and polymeric sugars into monosaccharides. The solid fraction was washed with water (0.5 dm3) and pressed. The obtained solid residue was weighed, sampled for dry matter determination, and the yield of solid residue (%) was calculated as the weight ratio of solid residue to the wheat straw weighed to the autohydrolysis treatment (100%*g dry wheat straw/g dry solid residue). Soluble phenolic substances in the liquid were determined using the Folin-Ciocalteu method with guiaiacol as standard.

Figure 11:
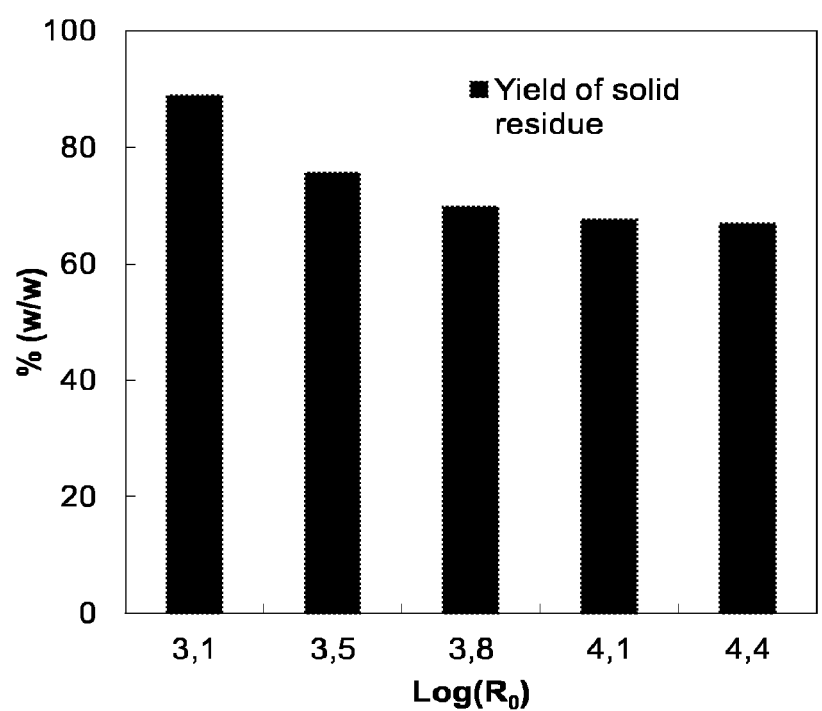
FIG. 11 presents yield of solid residue from autohydrolysis of wheat straw.
Figure 12:
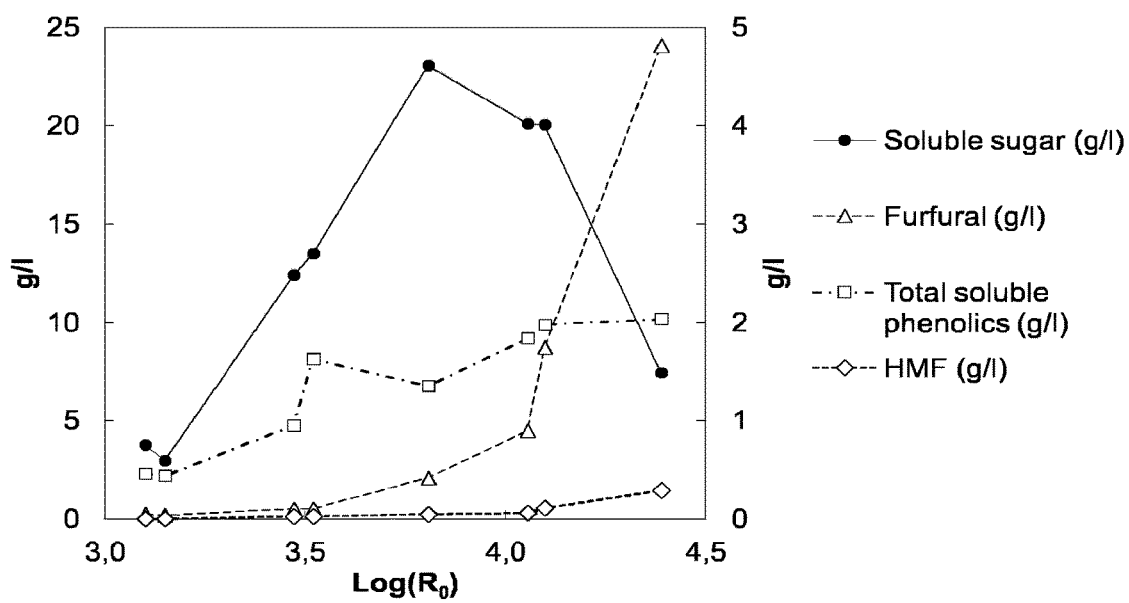
FIG. 12 presents the concentration of total soluble sugar (g/l, left y-axis) and potential microbial inhibitor substances; furfural, hydroxymethyl furfural (HMF) and soluble phenolics (g/l, right y-axis) in the liquid fraction obtained from autohydrolysis of wheat straw at 10% consistency (g straw solids dry matter/g total).

The results shown in FIG. 11 and FIG. 12 summarize the results. The yield of solid residue decreased with autohydrolysis severity with 67% yield at the highest severity (Log(R0)=4.4) (FIG. 11). The concentration of monosaccharide sugars in the liquid fraction first increased and then decreased with increasing autohydrolysis severity. The maximum concentration of sugar (23.1 g/l) was obtained when autohydrolysis severity was Log(R0)=3.8. Beyond this autohydrolysis severity the concentration of sugar in the liquid fraction drastically decreased and concentration of furfural and HMF suddenly increased reaching concentration of 4.8 g/l and 0.3 g/l, respectively. In contrast to the sudden generation of furfural and HMF, the concentration of soluble phenolics increased progressively from 0.5 g/l up to 2.0 g/l with increasing autohydrolysis severity.

This example shows that optimal autohydrolysis conditions in terms of autohydrolysis severity (Log(R0)) can be selected to avoid excess formation of furfural, HMF, and soluble phenolics while maximizing the concentration of monosaccharides in the liquid fraction.

Example 2

A suspension was prepared by mixing 33.8 kg chopped wheat straw containing 11% moisture with 350 kg of tap water giving consistency of 8.5%. The suspension was heated up to approximately 60° C., and the liquid fraction separated from the solids by filtration in an agitated Nutsche Filter. The solid fraction (31.2 kg dry matter) was mixed with water to give 192.4 kg of suspension at 5% consistency. The suspension was heated to 180° C. and cooled down to room temperature giving severity of S=4.15. The solid fraction was separated from the liquid fraction in a decanter centrifuge. The solid fraction was washed with water, and the washed insoluble fraction "autohydrolysed straw" (15.3 kg dry matter) was recovered using the decanter centrifuge and stored in freezer. Based on HPLC analysis, the liquid fraction (6.3 kg dry matter) contained hemicellulose-derived sugars approximately half of its dry matter.

The example shows that autohydrolysis enables separation of hemicellulosic sugars from lignocellulosic material before the enzymatic hydrolysis of the solid fraction containing cellulose.

Separation of the liquid and solid fraction and optional washing of the solid fraction separates soluble phenolic substances and organic acids released in autohydrolysis from the autohydrolysed solid fraction. As a result, consumption of alkaline delignification chemical in the subsequent delignification step is synergistically decreased.

The solid fraction produced from this experiment was used subsequently in the delignification tests, which resulted in solid fraction with low lignin and high carbohydrate content.

Example 3

A suspension was prepared by mixing 10.5 kg of milled straw at 7.3% moisture and 54.1 kg of tap water in a 100 dm3 container. After storing at room temperature for 18 h, 64.2 kg of the suspension was weighed into a horizontal cylindrical 250 dm3 stirred autoclave reactor. The reactor was closed and heated within 75 min to 140° C., maintained at 140° C. for 5 h and cooled to room temperature within 30 min. The hydrothermally treated suspension was removed from the reactor, and liquid and solid fractions were separated by filtration. The solid fraction was washed with tap water and pressed using a hydro-press. The pressed solid fraction (20.9 kg) had 42.7% dry matter content.

The solid fraction produced from this experiment was used subsequently in the delignification tests, which resulted in solid fraction with low lignin and high carbohydrate content.

Delignification of Autohydrolyzed Straw

Autohydrolysed straw contains considerable amounts of lignin that causes inhibitory effects in the enzymatic hydrolysis. For this reason the solid material from auto hydrolysis is extracted in alkaline conditions to remove lignin prior to enzymatic hydrolysis.

Example 4

A suspension was prepared by mixing 20.5 kg (8 kg dry matter) of autohydrolysed straw from the Example 2 with 262 g granular NaOH and tap water in a 180 dm3 stainless steel reactor equipped with a stirring unit. The suspension at 6.6% consistency was treated by heating the reactor to 95° C. in in 30 min followed by isothermal treatment at 95° C. for 1 h with continuous stirring. The extracted solid fraction was separated from the liquid fraction by filtration in a centrifuge, washed with tap water, pressed and the NaOH-extracted AH-straw (23.64 kg, 27% dry matter content) was stored in 6° C. The liquid fraction ("NaOH delignification solution") containing 1.62 kg dissolved material from autohydrolysed straw was stored at 6° C.

Enzymatic hydrolysis of the NaOH-extracted AH-straw with an enzyme dose of 35 µl/g Flashzyme Plus (Roal Oy, Finland), which was equal to 6 FPU (filter paper unit)/g DM of cellulase activity, gave 65.0% sugar yield from autohydrolysed straw carbohydrates. This is an improved result compared to 61.0% sugar yield from autohydrolysed straw carbohydrates without delignification.

The sugar yield is calculated as the ratio of total amount of monosaccharides released in enzymatic hydrolysis of NaOH-extracted AH-straw to total amount of mosaccharides released from similar weight of AH-straw in acid hydrolysis multiplied with the dry matter yield of NaOH-extracted AH-straw from the delignification treatment This example shows that the same enzyme amount produces higher yield of sugar in enzymatic hydrolysis, when lignin is removed before the enzymatic hydrolysis by alkaline treatment (NaOH). The example also shows that part of the lignin is dissolved in alkaline liquid fraction and that the lignin can be recovered by precipitation.

Example 5

A suspension at 3.6% consistency was prepared by mixing autohydrolysed straw from the Example 2 (403 g, 156 g dry matter) with 4050 g tap water and 37.5 g solid $Na_2CO_3$ in a glass reactor equipped with a magnetic stirrer. The reactor was heated up to 95-100° C. in 30 min and treated for 4 h at 95-100° C. with continuous stirring of the suspension. 812 g of Na2CO3-extracted solid fraction ("Na2CO3-extracted AH-straw") having a 15% dry matter content was separated from the liquid fraction (3325 g) by filtration, washed with tap water, pressed and stored in 6° C. The yield of the solid fraction (DM of delignified straw/DM of autohydrolysed straw) was 78%. The liquid fraction (Na2CO3 delignification solution) had pH 9.8 and was stored at 6° C. The amount of used carbonate is higher that NaOH since the carbonate is a weaker base than the hydroxide.

Enzymatic hydrolysis of Na2CO3-extracted AH-straw with an enzyme dose of 35 µl/g Flashzyme Plus (Roal Oy, Finland), which was equal to 6 FPU (filter paper unit)/g DM of cellulase activity, gave 59.1% sugar yield from autohydrolysed straw carbohydrates. This was less than 65.0% sugar yield with NaOH-extracted AH-straw from autohydrolysed straw carbohydrates or 61.0% sugar yield from autohydrolysed straw carbohydrates without delignification.

The sugar yield is calculated as the ratio of total amount of monosaccharides released in enzymatic hydrolysis to total amount of monosaccharides released from similar weight of AH-straw in acid hydrolysis multiplied with the dry matter yield of Na2CO3-extracted AH-straw from the delignification treatment.

Compared to autohydrolysed straw that was subjected to enzymatic hydrolysis without delignification, advantage of the Na2CO3-delignification was that additional lignin fraction (Na2CO3 delignification solution) was obtained.

This example shows that the same enzyme amount produces higher yield of sugar in enzymatic hydrolysis, when lignin is removed before the enzymatic hydrolysis by alkaline treatment ($Na_2CO_3$). The example also shows that part of the lignin is dissolved in alkaline liquid fraction and that the lignin can be recovered by precipitation

Example 6

A suspension was prepared by mixing 10.0 kg (4.41 kg dry matter) of autohydrolysed straw from the Example 3 with tap water (29.5 kg) and 3.401 g of 50% (w/w) aqueous NaOH. The suspension was treated in similar reactor and thermal conditions as described above in Example 3. The solid fraction ("NaOH-delignified straw"), was separated by filtration, and after washing had 30.4% dry matter content. The liquid fraction ("NaOH delignification solution") had pH 13.0 and was stored in 6° C.

Example 7

The purpose of the example was to study the effect of alkaline treatment of autohydrolysed straw on enzymatic hydrolysis and sugar yield from autohydrolysed straw. To achieve this, a suspension at 7.5% consistency was prepared by mixing 15 g of dry matter of autohydrolysed straw from Example 1 with deionized water and chemicals listed in Table 1. The different alkaline chemicals were used to adjust pH before the heating to the indicated value. The suspension was heated rapidly to 90° C. in a microwave oven. The hot suspension was filtered to separate solid and liquid fractions. The solid fraction was washed with water and the filter cake stirred to homogeneity, and its dry matter content was measured. The washed solid fraction (10 g of dry matter) was hydrolysed with 350 µL (6 FPU/g) of cellulolytic preparation Flashzyme Plus (Roal, Finland) at 10% consistency in 0.05 M Na-acetate buffer at pH 5 in presence of potassium sorbate. Hydrolysis was carried out in 250 mL conical flask placed in a thermostatic incubator set at 50° C. reaction continued with 200 rpm shaking for 72 h. Released monomeric sugars were determined from the liquid fraction by HPLC. The obtained dry matter and sugar yields are presented in Table 1.

The example shows that delignification of autohydrolysed straw increases the sugar yield from the autohydrolysed straw by enzymatic hydrolysis even when dry matter losses in delignification treatment are taken into account. Another advantage of the delignification treatment is generation of soluble lignin fraction suitable for further processing.

Surprising finding of the example was that only a low amount of alkaline chemical is needed in delignification of autohydrolysed straw. Another surprising finding was that pH of the liquid fraction isolated from the delignified solid fraction was relatively low which means that lower amount of acid is needed to precipitate lignin from the solution by decreasing the pH.

Examples on Enzymatic Hydrolysis of Autohydrolysed and/or Delignified Straw

Example 8

A comparison of NaOH-delignified straw (material from the Example 6) and autohydrolysed straw (material from the Example 1) was performed in three different enzyme hydrolysis processes, including batch hydrolysis, sequential hydrolysis and solids-recycling at a constant process feed. An enzyme mixture was used, comprising 85% cellulase (Econase CE, Roal Oy), 10% cellobiase (Novozyme 188, Sigma/Novozymes) and 5% xylanase (GC140, Genencor). Reactions were performed at pH 5 and at temperature of 50° C. in a shaker at 200 rpm.

Batch Hydrolysis

Figure 6:
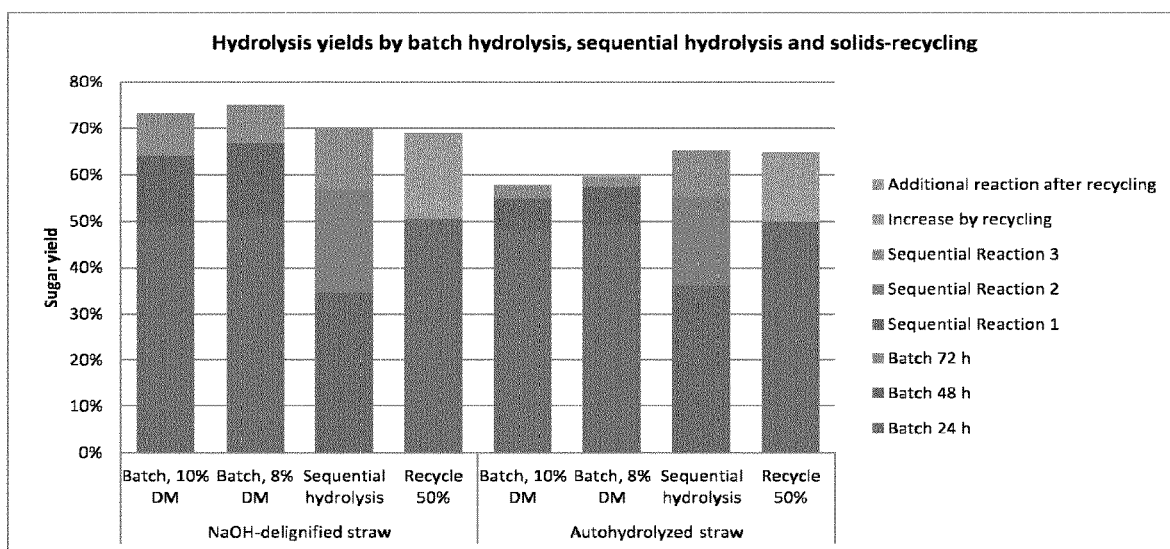
FIG. 6 presents total sugar yields from NaOH-delignified straw and autohydrolysed straw in batch hydrolysis after 24 h, 48 h and 72 h, after the 1st, 2nd and 3rd sequential hydrolysis and after solids recycling and an additional 24 h reaction.

A batch hydrolysis was performed to NaOH-delignified straw and autohydrolysed straw at 10% consistency and at 8% consistency (where "consistency" was the proportion of insoluble solids in the reaction slurry, w/w). An enzyme dose was used that contained an enzyme activity of 9 FPU/g pretreated straw DM. The sugar yields (the released anhydrous sugars as percentage of the total polymeric carbohydrates in the material), are shown in FIG. 6. After 24 h, 48 h and 72 h of hydrolysis, the sugar yields from NaOH-delignified straw at 8% and 10% consistency averaged 50%, 65% and 74%, whereas with autohydrolysed straw, the yields at 8% and 10% consistency averaged 49%, 56% and 59%, respectively, showing that a higher sugar yield can be obtained from NaOH-delignified straw with the same enzyme amount than from autohydrolysed straw. The yields were generally slightly higher at the lower consistency.

Figure 8:
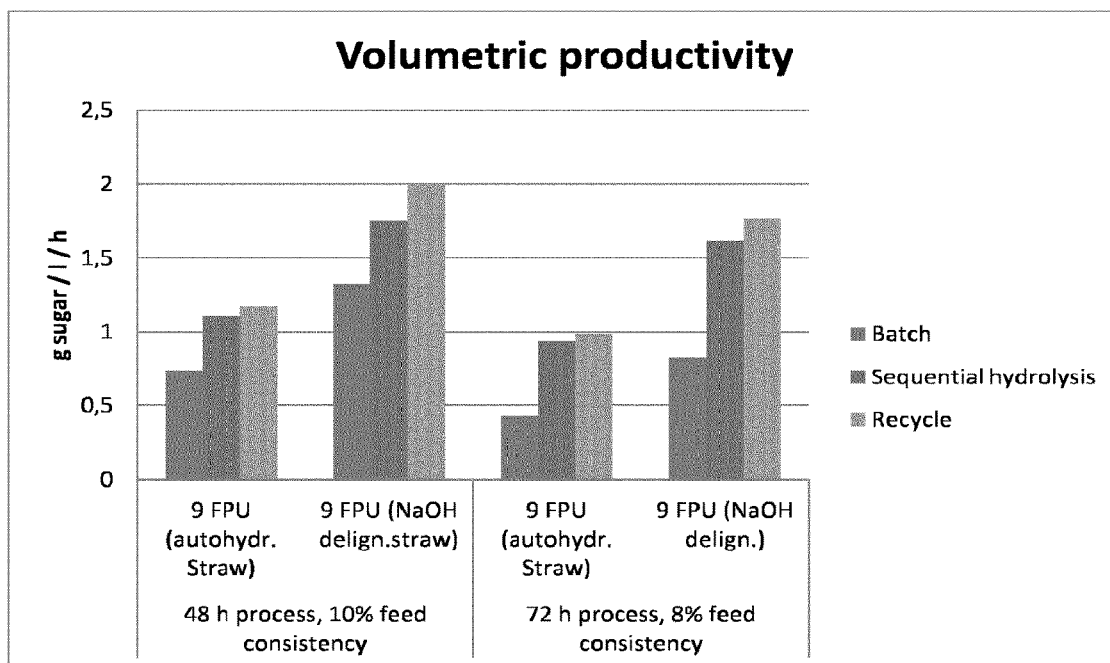
FIG. 8 presents the volumetric sugar productivities of batch hydrolysis, sequential hydrolysis and solids-recycling.

The volumetric productivity shown in FIG. 8 of the 48 h and 72 h batch hydrolysis of NaOH-deliginified straw was 1.32 g/l/h (grams of sugar per litre of the reaction slurry per hour) and 0.82 g/l/h, respectively, which were considerably higher compared the volumetric productivities of 0.74 g/l/h and 0.42 g/l/h, respectively, obtained from autohydrolysed straw.

Figure 7:
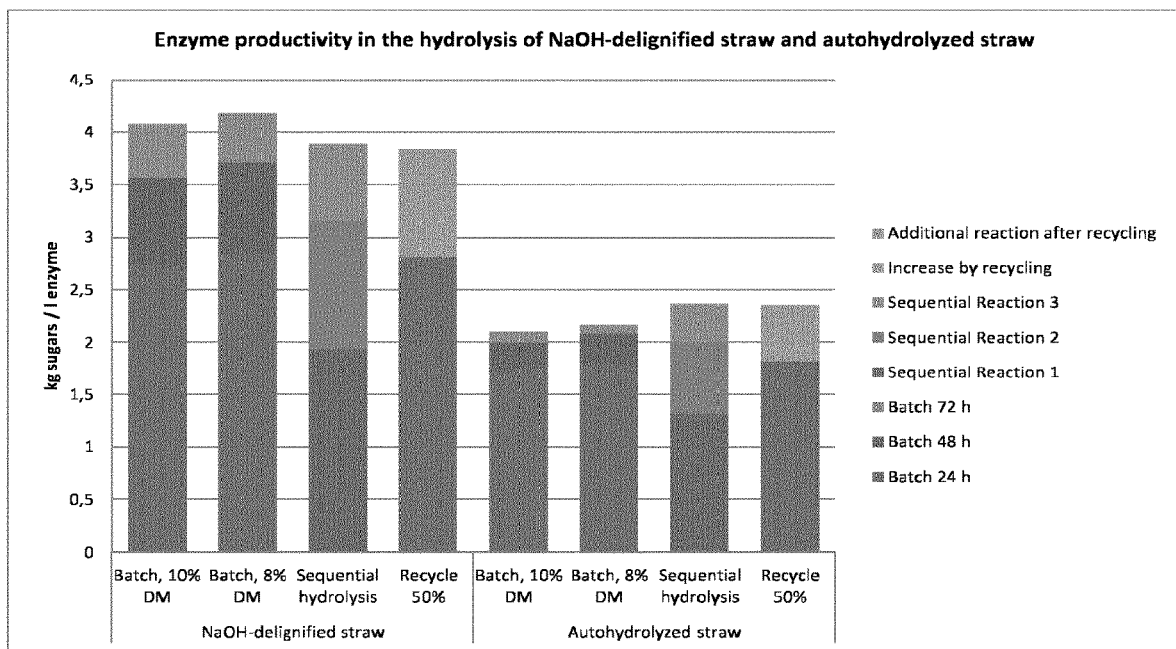
FIG. 7 presents enzyme productivities in the hydrolysis of NaOH-delignified straw and autohydrolysed straw in batch hydrolysis, sequential hydrolysis and solids recycling.

The enzyme productivity (kg sugar obtained with a litre of enzyme) of the reactions is shown in FIG. 7. The enzyme productivity in the 72 h batch hydrolysis of NaOH-delignified straw was 4.2 kg/l enzyme which was almost double compared to the 2.2 kg/l enzyme productivity with autohydrolysed straw.

This example indicates that a higher sugar yield, enzyme productivity and volumetric productivity was obtained from delignified straw compared to autohydrolysed straw in a batchwise enzymatic hydrolysis.

Sequential Hydrolysis

NaOH-delignified straw and autohyrolysed straw were hydrolysed by a three-step hydrolysis that consisted of three sequential 24 h reactions. Between the reactions, liquid was separated from the solids and the solid residue was mixed with fresh liquid and enzymes. The proportion of solids in the total process ("the total consistency" or "the feed consistency") was 10% in the first two reactions and 8% in the three reactions. Because the total liquid amount was divided between the reactions, the actual consistency of the first, second and third reaction were 14.3%, 12.5% and 10.6% with NaOH-delignified straw and 14.4%, 12.9% and 12.8% with autohydrolysed straw, respectively. Similar enzyme cocktail and dose were used, as described in "batch hydrolysis of NaOH-delignified straw." Two thirds (66.6%) of the total enzyme dose was applied in the first reaction and one third (33.3%) in the second reaction.

The sugar yield (the released anhydrous sugars as percentage of the total polymeric carbohydrates in the material, as shown in FIG. 6, after the first, the second and the third reaction was 35%, 57% and 70%, respectively, from NaOH-delignified straw and 36%, 55% and 65%, respectively, from autohydrolysed straw. Although the yield was slightly higher from autohydrolysed straw after the first reaction, the yield from NaOH-delignified straw clearly prevailed after the second and third reactions. The total volumetric productivity (FIG. 8) after two and three sequential 24 h reactions was 1.74 g/l/h and 1.61 g/l/h, respectively, with NaOH-delignified straw, which was considerably higher compared to the productivities of 1.10 g/l/h and 0.94 g/l/h, respectively, from autohydrolysed straw. The enzyme productivity after three 24 h reactions with NaOH-delignified straw was 4.4 kg/l enzyme, which was drastically higher compared to the enzyme productivity of 2.4 kg/l with autohydrolysed straw (FIG. 7).

This example indicates that a higher sugar yield, enzyme productivity and volumetric productivity was obtained from delignified straw compared to autohydrolysed straw in a sequential enzymatic hydrolysis.

Hydrolysis with Solids-recycling

NaOH-delignified straw and autohydrolysed straw were hydrolysed in a solids-recycling process. Multiple subsequent reactions were performed, where fresh pre-treated straw, enzyme and liquid were mixed at 10% consistency. Into the mixture of fresh reaction constituents, 50% of the separated solid residue from the previous reaction was mixed. The recycling of the solid residue led to an increase in the actual reaction consistency, which was increased to 12.3% with NaOH-delignified straw and to 13.2% with autohydrolysed straw. Six subsequent recycling reactions were performed in order to reach a steady state, where the reaction volume, consistency and hydrolysis yield remained constant between subsequent reactions. When steady state was reached, the part of the solid residue that was not recycled was mixed with a constant amount of fresh liquid and an additional 24 h reaction was performed, at a consistency of 10.5% with NaOH-delignified straw and 13.1% with autohydrolysed straw. The total proportion of solids (or "the total consistency" or "the feed consistency") was 10% in the recycling reaction alone and 8% in the process including the recycle reaction and the additional reaction.

The sugar yield released as anhydrous sugars as percentage of the total polymeric carbohydrates in the material, FIG. 6. In the initial reaction that did not contain any recycled material was 51% and 50% for NaOH-delignified straw and autohydrolysed straw, respectively. After six subsequent reactions with 50% recycling of the solid residue, the hydrolysis yield was increased to 57% and 55% with NaOH-delignified straw and autohydrolysed straw, respectively. After the additional reaction the total sugar yield was 69% and 65% with NaOH-delignified straw and autohydrolysed straw, respectively, thus showing generally higher yields for NaOH-delignified straw. The volumetric productivity of the recycle reaction alone with NaOH-delignified straw and autohydrolysed straw was 1.99 g/l/h and 1.17 g/l/h, respectively, and including the additional reaction, 1.77 g/l/h and 0.99 g/l/h, respectively, showing considerably higher volumetric productivities with NaOH-delignified straw. The enzyme productivity of the recycle reaction alone with NaOH-delignified straw and autohydrolysed straw was 3.2 kg/l and 2.0 kg/l, respectively, and when the additional reaction was included, 3.8 kg/l and 2.4 kg/l, respectively, showing drastically higher enzyme productivity for NaOH-delignified straw compared to autohydrolysed straw.

Figure 9:
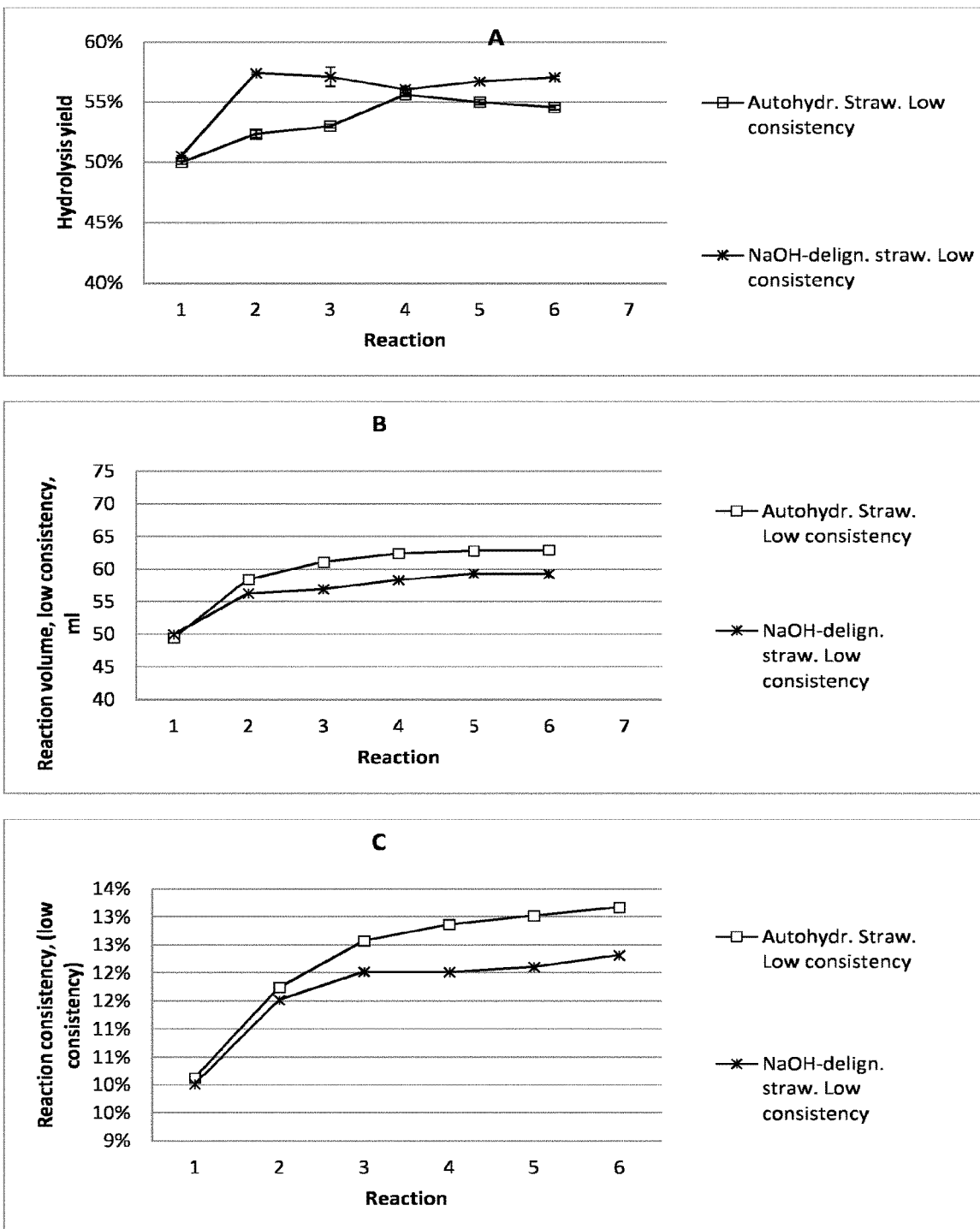
FIG. 9 presents progression of solids-recycling reactions with 50% recycle rate in terms of hydrolysis (A), reaction volume (B) and reaction consistency (C).
Figure 10:
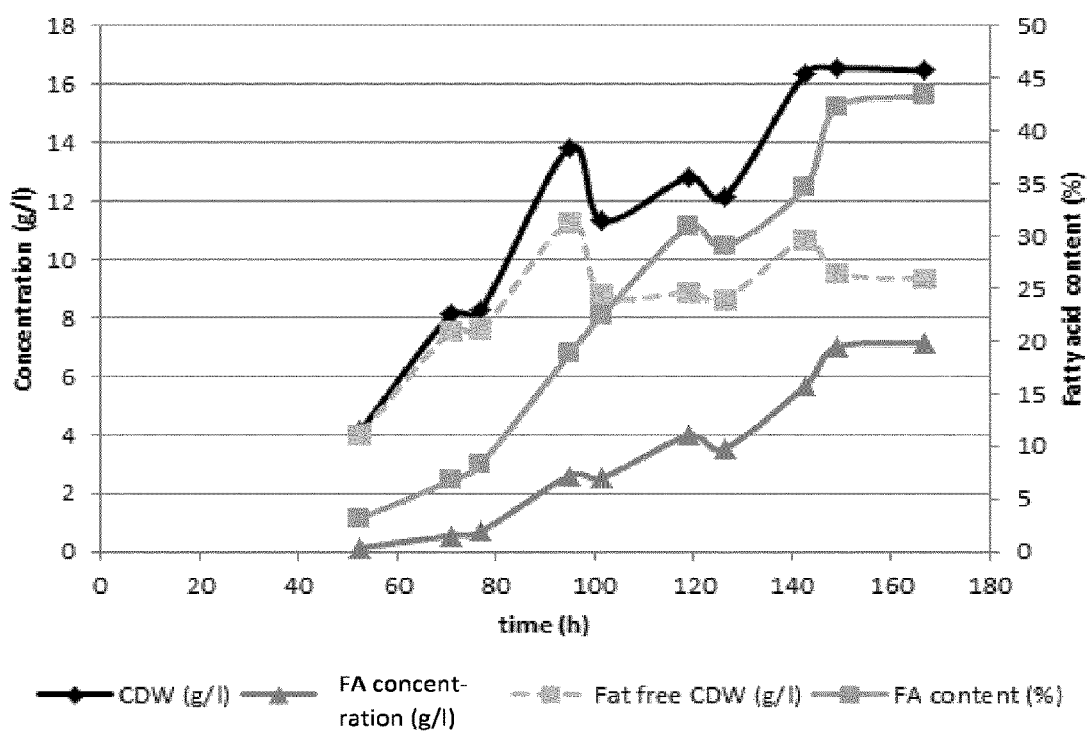
FIG. 10 presents results of fed-batch fermentation with *Aspergillus oryzae* on wheat straw hydrolysates.

The progression of the hydrolysis in the subsequent reactions is presented in FIG. 9a. The progression of the reaction volume is presented in FIG. 9b. The progression of the reaction consistency in presented in FIG. 9c.

This example indicates that a higher sugar yield, enzyme productivity and volumetric productivity were obtained from delignified straw compared to autohydrolysed straw in enzymatic hydrolysis process with solids recycling.

Conclusions of Example 8
1. The overall sugar yield was generally higher for NaOH-delignified straw compared to autohydrolysed straw in all different processes enzymatic hydrolysis.
2. Since the volumetric productivity was higher with NaOH-delignified straw compared to autohydrolysed straw in all different processes, smaller reactors and separators are required for a given sugar production rate in the hydrolysis of NaOH-delignified straw compared to autohydrolysed straw.
3. Since the enzymatic productivity was higher with NaOH-delignified straw compared to autohydrolysed straw in all different processes, the enzyme cost per kg of obtained sugar is lower with NaOH-delignified straw than with autohydrolysed straw.
4. Equal amounts of water per pre-treated straw were used in this example. It can be concluded that solids-recycling and sequential hydrolysis led to equal hydrolysis yields but increased the volumetric productivities compared to batch hydrolysis.

Example 9

Lignin Quality

Autohydrolysed straw (material from Example 2) was hydrolysed in a three-step sequential hydrolysis as described in example 8, at a 20% feed consistency with an enzyme dose of 9 FPU, with the enzyme cocktail described in example 9. A sugar yield (the released anhydrous sugars as percentage of the total polymeric carbohydrates in the material) of 64.4% was obtained, which was equal to 34.8% of autohydrolysed straw DM. The residual solids from the enzymatic hydrolysis comprised 27.2% of sugars, 55.5% of lignin and 8.8% of ash.

Autohydrolysed straw (Material from Example 2) (40.7 g dry matter) was extracted with aqueous 0.2 M NaOH. The extraction was carried out at 7.7% consistency in a stirred glass reactor refluxed at 95-100° C. for 4 h. The liquid fraction was separated from the extracted solid fraction by filtration. The obtained liquid fraction (657.6 g) was acidified with 12 M sulfuric acid to pH 4.9 in order to precipitate the dissolved lignin. The precipitated lignin was separated from the liquid fraction by centrifugation, washed with acidified water and lyophilized. The obtained lignin fraction accounted for 35.9% of the lignin originally present in autohydrolysed straw. The lignin fraction had total lignin content (sum of acid insoluble lignin and acid soluble lignin) of 90.9% and 4.0% ash compared to 55.5% lignin content and 8.8% ash content of the residual solids after enzymatic hydrolysis.

This example shows that advantage of the delignification treatment is optional isolation of solid lignin fraction that has notably higher lignin content compared to lignin content of the enzymatic hydrolysis residue. The higher purity of lignin is advantageous for the usage of lignin in higher value applications compared to combustion.

Use of Lignocellulosic Sugars for Production of Lipids

Example 10

Preparation of Hydrolysates
Autohydrolysis Liquid C

The autohydrolysis reaction for wheat straw and subsequent isolation of hemicellulose oligosaccharides was carried out to produce liquid fraction for fermentation, and solid fraction susceptible for enzymatic hydrolysis. To achieve this, 35.7 kg wheat straw (89.8% dry matter content) was mixed with 240 kg of water giving suspension at 11.6% consistency in a 500 dm3 stirred tank reactor. The suspension was heated up to 180° C. followed by cooling to below 100° C. The hydrothermally treated suspension was discharged from the reactor and the first liquid fraction separated from the solid fraction using a decanter centrifuge. The solid fraction was suspension-washed in acidic water adjusted to pH 4 with phosphoric acid. The solid fraction was separated from the second liquid fraction in the decanter centrifuge. The first and second liquid fractions were combined and concentrated in a falling film evaporator to give 18.3 kg of concentrated autohydrolysis liquid forming autohydrolysis liquid C containing hemicellulose sugars partly in oligomeric from and having 42% dry matter content and 38° Bx refractometric dry substance. The washed solid fraction (96.7 kg having 23.0% dry matter content) was used as feed material for enzymatic hydrolysis to produce cellulose hydrolysate for cultivation.

Part of the phenolic compounds the autohydrolysis liquid concentrate contained were removed by treating the liquid by adding 40 g/l activated carbon, mixing gently for 20 hours in 4 C and finally filtering the carbon away using 400 um filtration cloth.

Enzymatic hydrolysate from cellulose fraction of wheat straw was prepared from the solid fraction containing cellulose (after washing) from autohydrolysis experiment where autohydrolysis liquid C was prepared. The washed solid fraction from autohydrolysis treatment forming autohydrolysis liquid C (17.3 kg having 23.1% dry matter content) was weighed into a 40 dm3 stirred-tank reactor and mixed with 14.7 kg water and 10 mL 50% NaOH (w/w) to give suspension at 12.5% consistency and at pH 5. The reactor was heated up and maintained at 50° C. and 216 ml of enzyme mixture comprising 82% cellulose (Econase CE, Roal Oy), 10% cellobiase (Novozyme 188, Sigma/Novozymes) and 7% xylanase (GC140, Genencor). During the enzymatic treatment the suspension was stirred periodically three times per hour for 5 min. After 48 h residence time the suspension was supplemented with fresh enzyme mixture amounting 10% of the initial enzyme dosage and having similar proportions of individual enzymes. After 72 h residence time at 50° C. the liquid fraction was separated from the solid fraction by filtration using a hydropress. The solid fraction was washed once with water and the liquid fraction again separated from the solid fraction. The liquid fractions were combined and concentrated by evaporation under reduced pressure. The cellulosic hydrolysate concentrate (1.57 kg) contained 220 g/l total sugar.

The cellulose hydrosate containing monomeric sugars was used as such in cultivation.

Single Cell Oil Production

The experiments were done using a lipid producing fungal strain *Aspergillus oryzae*. From the sporulating fungus grown on PDA-plates a spore suspension was made by adding 12 ml of sterile water and the spores were scraped off with inoculation loop to the liquid. 24 ml of the spore suspension was directly used for fermenter inoculation. The medium composition is presented in table 5. Purified autohydrolysis liquid C (hemicellulose solution, hemicellulosic sugars) and the cellulose hydrolysate from the same experiment was used in the cultivation. The cultivation was done in Biostat B plus 5 l fermenter in 3 l volume, and during it the stirring was set to 500 rpm, pH was kept in 5.5 with 3 M NaOH, the aeration was 1 vvm and the temperature 35 C during growth, in lipid production it was lowered to 28 C.

TABLE 2

Composition of growth medium

| Medium components | Concentration (g/l) |
|---|---|
| Hemicellulosic sugars | 20 |
| Yeast extract | 2 |
| (NH4)2SO4 | 1.5 |
| MgCl*6H2O | 1.5 |
| K2HPO4 | 0.8 |
| KH2PO4 | 1.5 |
| CaCl2*2H2O | 0.3 |

After inoculation it took about 30 h before the fungus started growing actively. During cultivation, the hemicellulose solution was added in small batches, and after 95 h of cultivation the feeds were changed to cellulosic hydrolysate. During the cultivation, in total 236 g of hemicellulose and 484 g cellulose hydrolysate was added. Part of the sugars added was left unutilized at the end of the fermentation. At 167 h, when the cultivation ended, there was 16 g/l of biomass, of which 43% lipids. It could be concluded that producing microbial oil from wheat straw hemicellulose and cellulose sugars was successful.

Example 11

Producing Microbial Oil on Hemicellulosic Sugars

Preparation of Hydrolysate, Autohydrolysis Liquid D

A suspension was prepared by mixing 10.5 kg of milled wheat straw (92.7% dry matter content) and 54.1 kg of tap water in a 100 dm3 container. After storing at room temperature for 18 h, 64.2 kg of the suspension was weighed into a horizontal cylindrical 250 dm3 stirred autoclave reactor. The reactor was closed and heated within 75 min to 140° C., maintained at 140° C. for 5 h and cooled to room temperature within 30 min. The hydrothermally treated suspension was manually discharged from the reactor, and the first liquid fraction was separated from the first solid by filtration. The first solid fraction was washed twice with tap water and pressed using a hydro-press giving washed solid fraction. The washed solid fraction (20.9 kg) had 42.7% dry matter content. The first liquid fraction was combined with the wash-waters and concentrated in a falling film evaporator to 11.5% (w/w) dry matter content. The concentrated liquid, autohydrolysis liquid D, contained 49.3% total sugar from the total dry matter of the concentrated liquid as determined after dilute acid hydrolysis (4% w/w sulfuric acid, 121° C., 1 h) by high-performance liquid chromatography (HPLC). The relative proportions of anhydrous xylose, anhydrous arabinose, anhydrous glucose, and anhydrous galactose of the total sugar content were 57%, 19%, 13%, and 11%, respectively.

After this the autohydrolysis liquid D containing hemicellulosic sugars partly in oligomeric form was used in cultivation experiments as such without purification.

Single Cell Oil Production

The experiments were done using a lipid producing fungal strain *A. oryzae*. From the sporulating fungus grown on PDA-plates a spore suspension was made by adding 12 ml of sterile water and the spores were scraped off with inoculation loop to the liquid. 24 ml of the spore suspension was used for inoculation of 6 flasks. The medium composition is presented in table 3. The inoculated flasks were incubated at 30 C 160 rpm shaking for 1 day, and then used for fermenter inoculation.

TABLE 3

Composition of inoculation medium, pH set to 5.5.

| | g/l |
|---|---|
| Hemicellulosic sugars | 40 |
| Yeast extract | 1 |
| (NH4)2SO4 | 1 |
| MgSO4*7H2O | 1 |
| K2HPO4 | 0.5 |
| KH2PO4 | 1 |
| CaCl2*2H2O | 0.2 |

Autohydrolysis liquid D (containing hemicellulosic sugars partly in oligomeric form) was used and it contained 4.2 g/l phenolic compounds based on analysis with Folin-Ciocalteu method (Waterhouse, 2002). The cultivation was done in Biostat B plus 5 l fermenter in 3 l volume, and during it the stirring was set to 400 rpm, pH was kept in 5.5 with 3 M NaOH, the aeration was 1 vvm and the temperature 30 C. The medium composition is presented in table 4.

TABLE 4

| The composition of fermentation medium | |
|---|---|
| Medium components | Concentration (g/l) |
| Hemicellulosic sugars | 60 |
| Yeast extract | 1 |
| (NH4)2SO4 | 1 |
| MgCl*6H2O | 1.0 |
| K2HPO4 | 0.5 |
| KH2PO4 | 1.0 |
| CaCl2*2H2O | 0.2 |

Results:

During cultivation, the hemicellulosic solution was added in small batches. In total 150 g of hemicellulose was added. Part of the sugars added was left unutilized at the end of the fermentation. At 142 h, when the cultivation ended, there was 14 g/l of biomass, of which 21% lipids. It could be concluded that producing microbial oil from wheat hemicellulosic sugars (partly in oligomeric form) was successful. Microbial oil production from hemicellulosic sugars was successful without the purification of the hydrolysate (other than evaporation used in the concentration of sugars). In the fermentation the concentration of phenolic compounds was 2.8 g/L.

The invention claimed is:

1. Method for fractionation of a lignocellulosic material, the method comprising:
   a) Subjecting the lignocellulosic material to an autohydrolysis treatment wherein hemicellulose is at least partially removed from the lignocellulosic material to produce a mixture containing a first liquid phase and a first solid phase;
   b) Separating the first solid phase from the first liquid phase;
   c) Subjecting the first solid phase to a delignification treatment in a presence of alkaline delignification agent to produce a mixture containing a second solid phase and a second liquid phase containing solubilized lignin, wherein delignification takes place without steam explosion, and wherein the concentration of delignification agent is from 0.1 to 10 wt %, based on the amount of dry matter in first solid phase;
   d) Separating the second solid phase from the second liquid phase; and
   e) Subjecting the second solid phase to an enzymatic hydrolysis treatment in a presence of enzymes capable of hydrolyzing hemicellulose and cellulose fractions of the second solid phase to produce a mixture containing a third liquid phase and a third solid phase, and
   wherein the lignin is precipitated from the second liquid phase by lowering a pH of a mixture and the precipitated lignin is recovered by a separation method which includes filtration, and wherein the second solid phase is not treated with any acid prior to enzymatic hydrolysis.

2. The method according to claim 1, wherein the alkaline delignification agent is selected from a group consisting of: sodium hydroxide, sodium carbonate, potassium hydroxide, potassium carbonate, calcium hydroxide, calcium carbonate, lithium hydroxide, lithium carbonate, ammonium hydroxide, ammonia, sodium sulphide, and the corresponding hydrates.

3. The method according to claim 1, wherein the alkaline delignification agent is added to the first solid phase to obtain a suspension having a pH of above 7.

4. The method according to claim 1, wherein the autohydrolysis treatment is conducted in conditions corresponding to severity of between 2.0 and 4.5.

5. The method according to claim 1, wherein the first solid phase is subjected to a steam explosion before said delignification treatment.

6. The method according to claim 1 comprising:
   a step of concentrating the third liquid phase.

7. The method for production of microbial lipid according to claim 1, the method comprising:
   a) subjecting the lignocellulosic material to a treatment wherein hemicellulose is at least partially removed from the lignocellulosic material to produce a mixture containing a first liquid phase and a first solid phase;
   b) separating the first solid phase from the first liquid phase;
   c) subjecting the first solid phase to a delignification treatment in a presence of alkaline delignification agent to produce a mixture containing a second solid phase and a second liquid phase containing solubilized lignin;
   d) separating the second solid phase from the second liquid phase; and
   e) subjecting the second solid phase to an enzymatic hydrolysis treatment to hydrolyze hemicellulose and cellulose fractions of the second solid phase to produce a mixture containing a third liquid phase of enzymatic hydrolysate and a third solid phase.

8. The method according to claim 1, wherein the concentration of delignification agent is from 0.1 to 4 wt %, based on the amount of dry matter in first solid phase.

9. The method according to claim 1, wherein the alkaline delignification agent is added to the first solid phase to obtain a suspension having a pH of between 10 and 13.

10. The method according to claim 1, wherein the autohydrolysis treatment is conducted in conditions corresponding to severity of between 3.0 and 4.1.

11. The method according to claim 1, wherein the autohydrolysis treatment is conducted in conditions corresponding to severity of between 3.5 and 4.0.

12. A method for production of microbial lipid, the method comprising:
   (i) providing a cultivation medium containing the third liquid phase produced in the method of claim 1;
   (ii) providing a fermentation broth by inoculating the cultivation medium with an oleaginous microbe;
   (iii) incubating said medium inoculated with said oleaginous microbe allowing lipid to accumulate; and
   (iv) recovering the lipid from said oleaginous microbe.

* * * * *